United States Patent
Wiggermann et al.

(10) Patent No.: US 12,029,480 B2
(45) Date of Patent: Jul. 9, 2024

(54) VISION SCREENING SYSTEMS AND METHODS

(71) Applicant: Welch Allyn, Inc., Skaneateles Falls, NY (US)

(72) Inventors: Neal E. Wiggermann, Batesville, IN (US); Eric J. Laurin, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 566 days.

(21) Appl. No.: 17/307,488

(22) Filed: May 4, 2021

(65) Prior Publication Data
US 2021/0345872 A1 Nov. 11, 2021

Related U.S. Application Data

(60) Provisional application No. 63/020,809, filed on May 6, 2020.

(51) Int. Cl.
*A61B 3/032* (2006.01)
*A61B 3/00* (2006.01)

(52) U.S. Cl.
CPC ............ *A61B 3/032* (2013.01); *A61B 3/0008* (2013.01); *A61B 3/0033* (2013.01); *A61B 3/0041* (2013.01); *A61B 2562/0219* (2013.01); *A61B 2562/227* (2013.01)

(58) Field of Classification Search
CPC ..... A61B 3/032; A61B 3/0008; A61B 3/0033; A61B 3/0041; A61B 2562/0219; A61B 2562/227; A61B 3/103
USPC ...................................................... 351/239
See application file for complete search history.

(56) References Cited

U.S. PATENT DOCUMENTS

| | | | | |
|---|---|---|---|---|
| 5,568,209 | A * | 10/1996 | Priester | A61B 3/032 351/239 |
| 9,155,466 | B2 * | 10/2015 | Su | A61B 5/0013 |
| 9,179,840 | B2 * | 11/2015 | Su | A61B 3/158 |
| 2019/0082951 | A1 * | 3/2019 | Merriam | A61B 3/032 |

(Continued)

FOREIGN PATENT DOCUMENTS

| | | |
|---|---|---|
| CN | 208598366 | 3/2019 |
| CN | 109924941 | 6/2019 |
| DE | 102008060909 | 6/2009 |

OTHER PUBLICATIONS

"Portable Green Laser Line and Cross Projector (515NM 30 MW) With Battery and Plugtop Charger", ODIC Force Lasers, link: https://odicforce.com/Portable-Green-Laser-Line-and-Cross-Projector-515nm-30mW-with-Battery-and-Plugtop-Charger, Retrieved on Nov. 29, 2019, p. 1.

*Primary Examiner* — Mohammed A Hasan
(74) *Attorney, Agent, or Firm* — Lee & Hayes, P.C.

(57) ABSTRACT

A system includes a base, and an emitter including a light source operable to generate a beam of visible radiation. The beam of radiation impinges a substantially horizontal support surface at a location approximately three meters from the emitter when the base is disposed on the support surface and the emitter is supported by the base. The system also includes a vision screening device supported by the base, the vision screening device having a first display, and a second display opposite the first display and facing the location. The system further includes a controller operable to cause the second display to output an image included in a visual acuity examination based at least in part on generation of the visible beam.

28 Claims, 6 Drawing Sheets

(56) References Cited

U.S. PATENT DOCUMENTS

2021/0065856 A1* 3/2021 Meyerson ............... H04L 67/12
2022/0248954 A1* 8/2022 Hunter ................. G06T 7/0012

* cited by examiner

VISION SCREENING SYSTEMS AND METHODS

CROSS-REFERENCE TO RELATED APPLICATION

This application is a U.S. Nonprovisional Applications of, and claims priority to, U.S. Provisional Application No. 63/020,809, filed May 6, 2020, the entire disclosure of which is incorporated herein by reference.

TECHNICAL FIELD

This application is directed to medical equipment, and in particular, to systems and methods associated with determining refractive error, convergence, visual acuity, and/or other parameters.

BACKGROUND

Visual screening in children and adults typically includes one or more tests to determine various deficiencies associated with the patient's eyes. Such vision tests may include, for example, refractive error tests, convergence tests, accommodation tests, visual acuity tests, and the like. While one or more of the above tests may be related, each test has a respective purpose. For instance, visual acuity testing typically relies on a person reading characters printed on a Snellen chart at a given distance. That person's visual acuity is based on which size of characters on the chart the person can discern. Once the person is positioned approximately three meters from the chart, the test usually begins with the person reading the top-most, largest character while covering one eye. While staying approximately three meters from the chart, the person proceeds to read each character in each line until they are no longer able to discern the characters. The process repeats for the opposite eye. A person with "normal vision" of 20/20 will read about 30 characters on the Snellen chart for each test.

In a refractive error test, on the other hand, the person is typically positioned approximately one meter or less from a vision screening device. Once the person is properly positioned, the screening device can be used to direct light onto the person's retinas. Sensors on the device may then collect corresponding light that is reflected by the retinas, and the device may determine a refractive error of each retina based on characteristics of the reflected light.

While various vision screening devices exist, such devices are typically cumbersome and complicated to use. Additionally, although the visual acuity test, the refractive error test, and other vision tests generally require different respective distances between the person being tested and the device being used for the test, existing vision screening devices are not configured to accurately determine the person's position, or to indicate where the person should be positioned relative to the device to ensure accurate testing results. Identifying these different distances can be difficult for some vision screening device users, particularly users that are responsible for performing vision tests in multiple different examination rooms or other vision screening environments. As a result, vision screening determinations made using existing devices may lack accuracy and consistency.

The various examples of the present disclosure are directed toward overcoming one or more of the deficiencies noted above.

SUMMARY

In an example of the present disclosure, a system includes a base, and an emitter including a light source operable to generate a beam of visible radiation. The beam of radiation impinges a substantially horizontal support surface at a location approximately three meters from the emitter when the base is disposed on the support surface and the emitter is supported by the base. The system also includes a vision screening device supported by the base, the vision screening device having a first display, and a second display opposite the first display and facing the location. The system further includes a controller operable to cause the second display to output an image included in a visual acuity examination based at least in part on generation of the visible beam.

In another example of the present disclosure, a system includes memory, one or more processors, and computer-executable instructions stored in the memory. The instructions are executable by the one or more processors to perform operations including causing a light source of an emitter to generate a beam of visible radiation. In such an example, the beam of radiation is directed to impinge upon a substantially horizontal support surface, supporting the emitter, at a location, and the location is approximately three meters from the emitter when a base associated with the emitter is disposed on the support surface and the emitter is supported by the base. The instructions also include receiving a first input based at least in part on the beam impinging the support surface, and causing a display of a vision screening device to output an image included in a visual acuity examination based at least in part on the first input. The instructions further include receiving a second input based at least in part on the image, and determining a visual acuity of the patient based at least in part on the second input.

In still another example of the present disclosure, a method includes causing, with a controller, a light source of an emitter to generate a beam of visible radiation. In such an example, the beam of radiation is directed to impinge upon a substantially horizontal support surface, supporting the emitter, at a location, and the location is approximately three meters from the emitter when a base associated with the emitter is disposed on the support surface and the emitter is supported by the base. Such a method also includes receiving, with the controller, a first input based at least in part on the beam impinging the support surface, and causing, with the controller, a display of a vision screening device to output an image included in a visual acuity examination based at least in part on the first input. Such a method further includes receiving, with the controller, a second input based at least in part on the image, and determining, with the controller, a visual acuity of the patient based at least in part on the second input.

BRIEF DESCRIPTION OF THE DRAWINGS

Features of the present disclosure, its nature, and various advantages, may be more apparent upon consideration of the following detailed description, taken in conjunction with the accompanying drawings.

In the figures, the left-most digit(s) of a reference number identifies the figure in which the reference number first appears. The use of the same reference numbers in different figures indicates similar or identical items or features. The drawings are not to scale.

DETAILED DESCRIPTION

Figure 1:
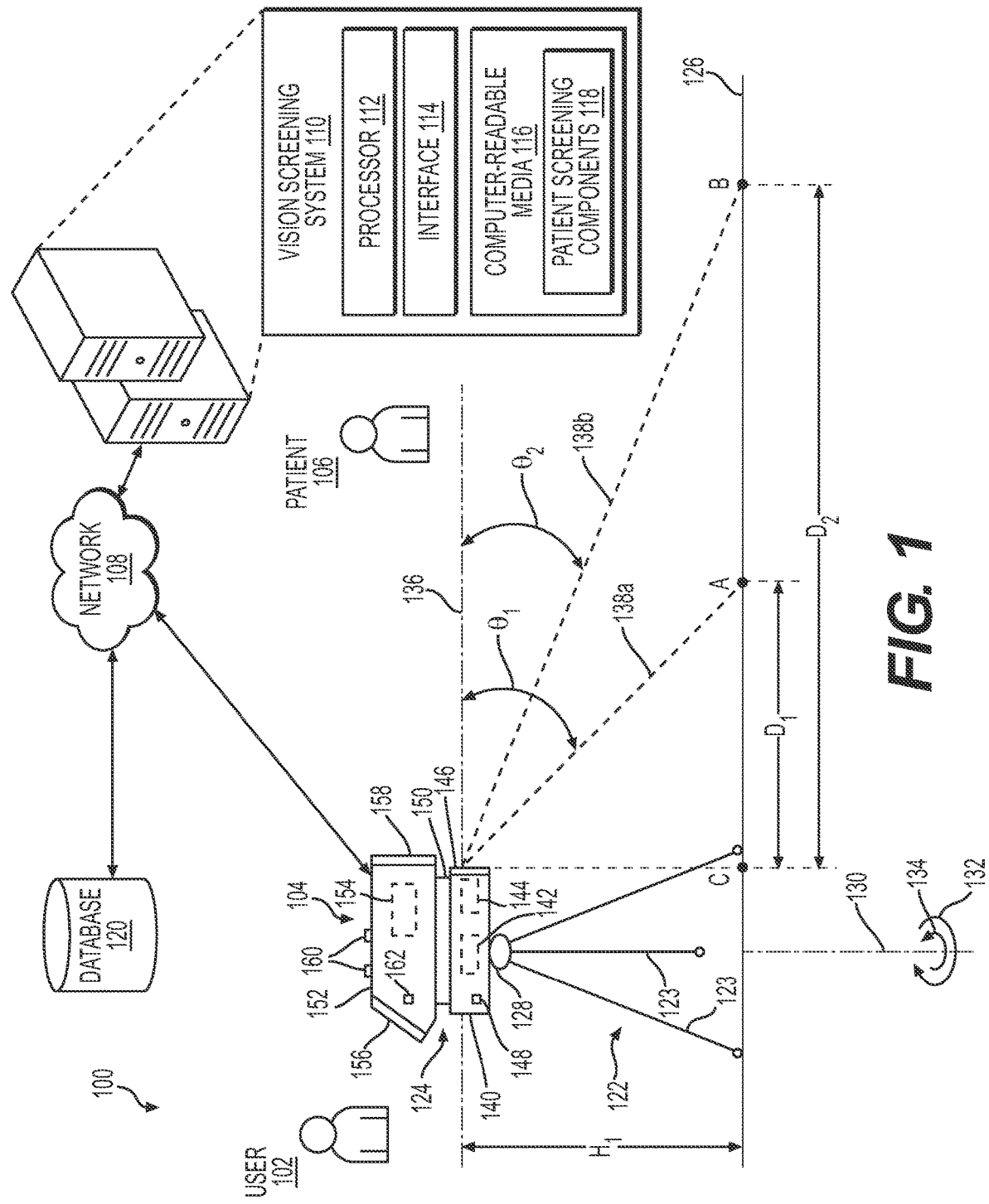
FIG. 1 illustrates an example system of the present disclosure. In some implementations, components of the example system shown in FIG. 1 may be used to perform one or more tests associated with vision screening.

The present disclosure is directed to, in part, a vision screening system and corresponding methods. Such an example vision screening system may be configured to perform one or more vision tests on a patient and to output the results of the vision test(s) to a user of the device, such as a physician or a physician's assistant. For example, the vision screening system may generate one or more graphical representations, such as a series of characters (e.g., a Snellen chart), images, or other items useful for testing the visual acuity of the patient. The system may also generate one or more beams of radiation, and may be configured to direct such beams at the retinas of the patient. The system may collect corresponding light that is reflected back from the retinas, and may determine a refractive error of the patient's eyes based at least in part on characteristics of the collected light. Moreover, the system may generate one or more paragraphs of text or a dynamic image, for display to the patient. While the patient is viewing such items, the system may collect one or more measurements associated with the eyes of the patient, such as a diameter of the lens of the eye, a location of the pupils, or a gaze of the patient. As such, in any of the examples described herein, the results of the various vision tests performed using the system may include one or more measurements obtained by the vision screening device included in the system. In addition, the system may generate a recommendation and/or diagnosis associated with the patient for display to the user of the vision screening device. For example, by utilizing standard testing data and/or machine learning techniques, the system may evaluate the measurements determined by the system to provide a recommendation to the user regarding the vision of the patient (e.g., whether the patient passed the test, requires additional screening, etc.). As such, the system described herein may provide automated diagnosis recommendations in order to assist the physician or other user of the vision screening device.

In any of the examples described herein, the various tests performed using a vision screening device may have respective distance requirement or other parameters that must be met in order to ensure accurate testing results. For instance, during a visual acuity test performed using a vision screening device of the present disclosure, it may be recommended that the patient be spaced from the vision screening device by approximately ten feet or approximately three meters. On the other hand, during a refractive error test performed using the same vision screening device, it may be recommended that the patient be spaced from the device by approximately three feet or approximately one meter. Accordingly, example systems of the present disclosure include a base configured to be disposed on a substantially planar and/or substantially horizontal support surface. Such example systems also include an emitter including at least one light source operable to generate a beam of visible radiation. Such a beam may comprise a beam of light having a wavelength in the visible band. In such examples, the emitter may be configured to direct the beam of radiation to impinge the support surface at a location corresponding to the particular vision test being performed. For example, when performing an acuity test, the emitter may direct a first beam to impinge the support surface at a location approximately three meters from the emitter when the base is disposed on the support surface and the emitter is removably attached to and/or otherwise supported by the base. When performing a refractive error test, on the other hand, the emitter may direct a second beam to impinge the support surface at a location approximately one meter from the emitter when the base is disposed on the support surface and the emitter is supported by the base. As will be described below, such distances (e.g., approximately three meters from the emitter, approximately one meter from the emitter, etc.) may comprise substantially linear distances measured from a location on the support surface aligned vertically below an emission face of the emitter to the location on the support surface at which the respective beams impinge the support surface. Such emitters may assist the physician or other user of the vision screening device with properly positioning the patient prior to performing the various vision tests described herein.

Additionally, in any of the examples herein, a system may include a vision screening device supported by the base. In some examples a housing of the vision screening device may be removably connected to a housing of the emitter. In other examples, the base described above may include a stem that is vertically, rotationally, and/or otherwise moveably connected to the base via a mount. In some examples, the vision screening device may be removably connected to the stem, and the emitter may be removably connected to the base via the mount. In other examples, the emitter may be removably connected to the stem, and the vision screening device may be removably connected to the emitter.

In still further examples, the one or more light sources of the emitter may be disposed within the housing of the vision screening device. In such examples, the housing of the vision screening device may be removably connected to the stem via a coupling. In some examples, such a coupling may include a first electrical connector configured to mate with a second electrical connector carried by the housing of the vision screening device. Such electrical connectors may assist in determining whether an acceptable vision screening device has been removably connected to the base for use in performing one or more vision tests. For instance, in examples in which an improper vision screening device (e.g., a vision screening device associated with an unapproved manufacturer) has been connected to the coupling, a controller of the system may provide a fault identification and/or may otherwise cause a visible and/or audible notification to be provided. Such a notification may indicate, for example, that an improper vision screening device has been connected to the coupling. Additionally or alternatively, the controller of the system may prohibit the emitter from generating one or more of the beams of visible radiation described above based at least in part on determining that an improper vision screening device has been connected to the coupling.

Additional details pertaining to the above-mentioned techniques are described below with reference to FIGS. 1-6. It is to be appreciated that while these figures describe example systems and devices that may utilize the claimed methods, the methods, processes, functions, operations, and/ or techniques described herein may apply equally to other devices, systems, and the like.

FIG. 1 illustrates an example system 100 for vision screening according to some implementations. As illustrated in FIG. 1, a user 102 may utilize a vision screening device 104 and/or other components of the system 100 to administer a vision screening test on a patient 106 to determine the vision health of the patient 106. As described herein, the vision screening device 104 may perform one or more vision screening tests to determine one or more measurements associated with the patient 106, and may provide the measurement(s), via a network 108, to a local or remote vision screening system 110 for analysis. In response, the vision screening system 110 may analyze the measurement(s) to diagnosis the vision health of the patient 106. It should be understood that, while FIG. 1 depicts the system 100 including a single vision screening system 110, in additional examples, the system 100 may include any number of local or remote vision screening systems substantially similar to the vision screening system 110, and configured to operate independently and/or in combination, and configured to communicate via the network 108. In examples, the vision screening system 110 may include one or more processors 112, one or more network interfaces 114, and/or computer-readable media 116. The computer-readable media 116 may store one or more programs, modules, engines, instructions, algorithms, and/or other patient screening components 118 that are executable by the processor(s) 112.

In examples, the vision screening device 104 may include a stationary or portable device configured to perform one or more vision screening tests on the patient 106. For example, the vision screening device 104 may be configured to perform a visual acuity test, a refractive error test, an accommodation test, dynamic eye tracking tests, and/or any other vision screening tests configured to evaluate and/or diagnose the vision health of the patient 106. Due to its stationary or portable nature, the vision screening device 104 may perform the vision screening tests at any location, from conventional screening environments, such as schools and medical clinics, to physician's offices, hospitals, eye care facilities, and/or other remote and/or mobile locations.

As described herein, the vision screening device 104 and/or vision screening system 110 may be configured to perform accommodation and refractive error testing on the patient 104. For example, refractive error and accommodation testing may include displaying a visual stimulus, such as a light or graphical representation, configured to induce a strain to the patient's 104 eyes. In response, the vision screening device 104 may detect the pupils and/or lenses of the eyes of the patient 104, acquire images and/or video data of the pupils/lenses, and the like, and may transmit the vision screening data, via the network 108, to the vision screening system 110 for analysis. Alternatively, or in addition, the vision screening device 104 may perform the analysis locally.

In examples, the vision screening device 104 may also be configured to perform visual acuity testing and/or dynamic eye tracking tests. For example, the vision screening device 104 and/or the vision screening system 110 may be configured to perform visual acuity testing, which includes determining an optotype, determining a distance of the patient 106 from the vision screening device 104, and/or displaying a static or dynamic optotype to the patient 104. The dynamic eye tracking test may include generating a graphical representation, such as a graphic scene or text, for display to the patient 106 and monitoring the movement of the eye, acquire images and/or video data of the eyes, and the like, and may transmit the vision screening data, via the network 108, to the vision screening system 110 for analysis. Alternatively, or in addition, in some examples, the vision screening device 104 may analyze the vision screening data locally. As will be described below, in any of the examples described herein, the system 100 may also include one or more emitters configured to generate beams of visible radiation (e.g., beams of light in the visible band) to assist with positioning the patient 106 relative to the vision screening device 104 (or vice versa). Such beams of visible radiation may, for example, be directed to imping a substantially horizontal support surface at various locations spaced from the vision screening device 104, and may be used to indicate locations at which the patient 106 should sit, stand, and/or otherwise be disposed during corresponding vision screening tests performed using the vision screening device 104.

In examples, a memory associated with the vision screening device 104 and/or one or more of the patient screening components 118 may be configured to store and/or access data associated with the patient 106. For example, the patient 106 may provide data (referred to herein as "patient data") upon initiating a vision screening test. For instance, when the vision screening device 104 and/or vision screening system 110 initiates a vision screening test, the patient 106 may provide, or the user 102 may request, patient data including the patient's demographic information, physical characteristics, preferences, and the like. For example, the patient 106 may provide demographic information such as name, age, ethnicity, gender, and the like. The patient 106 may also provide physical characteristic information such as height of the patient 106. In such examples, the user 102 may request the patient data while the screening is in progress, or before the screening has begun. In some examples, the user 102 may be provided with predetermined categories associated with the patient 106, such as predetermined age ranges (e.g., six to twelve months, one to five years old, etc.), and may request the patient data in order to select the appropriate category associated with the patient 106. In other examples, the user 102 may provide a free form input associated with the patient data. In still further examples, an input element may be provided to the patient 106 directly.

The vision screening device 104 may be configured to generate image and/or video data associated with the patient 106 at the onset of the vision screening test. For example, the vision screening device 104 may include one or more digital cameras, motion sensors, proximity sensors, or other image capture devices configured to collect images and/or video of the patient 106, and one or more processors of the vision screening device 104 may analyze the collected images and/or video to determine, for example, the height of the patient 106, the distance of the patient 106 from the screening device, and/or any of the patient data described above. For example, the vision screening device 104 may be equipped with a range finder, such as an ultra-sonic range finder, an infrared range finder, and/or any other proximity sensor that may be able to determine the distance of the patient 106 from the vision screening device 104.

Alternatively, or in addition, the vision screening device 104 may be configured to transmit the images, video, and/or any other collected information to the vision screening system 110, via the network 108, for analysis. In any such examples, the vision screening system may store such information in the computer-readable media 116 and/or in an external database 120. For example, the database 120 may comprise memory or other computer-readable media substantially similar to and/or the same as the computer-readable media 116. The database 120 may be accessible by the vision screening system 110, and/or by the vision screening device 104, via the network 108. In any such examples, the database 120 may be configured to store patient data in association with a patient ID (e.g., a name, social security number, an alphanumeric code, etc.) or other unique patient identifier. When the user 102 and/or patient 106 enters the patient ID, the patient screening component 118 may access or receive patient data stored in association with the patient ID.

Although not illustrated in FIG. 1, in some examples the computer-readable media 116 may additionally store a measurement data component. In such examples, the measurement data component may be configured to receive, access, and/or analyze testing data collected and/or detected by the vision screening device 104 during one or more vision screening procedures. For example, the measurement data component may be configured to receive, via the network 108, image data and/or video data generated by the vision screening device 104 during a vision screening test and while a graphical representation (e.g., a Snellen chart, a dynamic visual stimulus, etc.) is being displayed by the vision screening device 104. The measurement data component may analyze the image data and/or video data to determine one or more measurements associated with the patient 106, such as the gaze of the patient throughout the screening, a location of the patient's pupils at points in time of viewing the graphical representation, a diameter of the pupils, an accommodation of the lens, motion information associated with the eyes of the patient 106, and the like.

Further, although not illustrated in FIG. 1, the computer-readable media 116 may also be configured to store a threshold data component. The threshold data component may be configured to receive, access, and/or analyze threshold data associated with standard vision testing results. For example, in such embodiments, a threshold data component may be configured to access or receive data from one or more additional databases (e.g., the database 120, a third-party database, etc.) storing testing data, measurements, and/or a range of values indicating various thresholds or ranges within which testing values should lie. Such thresholds or ranges may be associated with patients having normal vision health with similar testing conditions. For example, for each testing category, standard testing data may be accessed or received by the threshold data component, and may be utilized for comparison against the measurement data stored by the measurement data component described above. For instance, the threshold data associated with the toddler testing category may include standard pupil measurements, and/or a threshold range of values which the testing values should not exceed or fall below (e.g., a standard value range) for toddlers when displayed each graphical representation. For example, when testing for accommodation in the patient 106, an example threshold data component may be configured to store information associated with the amplitude of accommodation and age (e.g., Donder's Table).

As used herein, the network 108 is typically any type of wireless network or other communication network known in the art. Examples of network 108 include the Internet, an intranet, a wide area network (WAN), a local area network (LAN), and a virtual private network (VPN), cellular network connections and connections made using protocols such as 802.11a, b, g, n and/or ac. U.S. Pat. No. 9,237,846, filed Feb. 17, 2012, describes systems and methods for photo refraction ocular screening and that disclosure is hereby incorporated by reference in its entirety.

As described herein, a processor, such as processor(s) 112, can be a single processing unit or a number of processing units, and can include single or multiple computing units or multiple processing cores. The processor(s) 112 can be implemented as one or more microprocessors, microcomputers, microcontrollers, digital signal processors, central processing units, state machines, logic circuitries, and/or any devices that manipulate signals based on operational instructions. For example, the processor(s) 112 can be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The computer-readable media 116 may can include volatile and nonvolatile memory and/or removable and non-removable media implemented in any type of technology for storage of information, such as computer-readable instructions, data structures, program modules, or other data. Such computer-readable media 116 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 116 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 116 can be used to store any number of functional components that are executable by the processor(s) 112. In many implementations, these functional components comprise instructions or programs that are executable by the processor(s) 112 and that, when executed, specifically configure the one or more processor(s) 112 to perform the actions associated with one or more vision tests.

The network interface(s) 114 may enable wired and/or wireless communications between the components and/or devices shown in system 100 and/or with one or more other remote systems, as well as other networked devices. For instance, at least some of the network interface(s) 114 may include a personal area network component to enable communications over one or more short-range wireless communication channels. Furthermore, at least some of the network interface(s) 114 may include a wide area network component to enable communication over a wide area network. Such network interface(s) 114 may enable, for example, communication between the vision screening system 110 and the vision screening device 104 and/or other components of the system 100, via the network 108.

With continued reference to FIG. 1, the system 100 may also include a base 122 configured to support components of the system 100 including the vision screening device 104. For example, the base 122 may include two or more legs 123 movably connected to a mount 128. As shown in FIG. 1, in some examples the base 122 may comprise a tripod, and the mount 128 may comprise a substantially rigid frame or other housing associated with the base 122. In such examples, a first end of each leg 123 may be hingedly, pivotably, or otherwise movably connected to the mount 128. Additionally, a second end of each leg, opposite the respective first end, may be configured to be supported by a support surface 126. As illustrated in FIG. 1, in some examples, the support surface 126 may comprise a substantially horizontal support surface 126 configured to support the base 122 and/or other components of the system 100. For instance, the support surface 126 may comprise a floor or other surface of a healthcare facility, screening center, or other location in which one or more components of the system 100 are disposed. Further, in some examples, one or more of the legs 123 may have a fixed length, while in other examples, each of the legs 123 may be extendable or may otherwise have a length that is adjustable in order to dispose the mount 128 and/or components of the system 100 supported by the base 122 at any desired vertical height above the support surface 126.

As shown in FIG. 1, in some examples the system 100 may also include an emitter 124. The emitter 124 may be removably connected to the mount 128 in any manner. For instance, the mount 128 may include one or more rails, channels, brackets, clamps, or other structures configured to mate with a corresponding rail, channel, bracket, clamp, ridge, or other structure of the emitter 124. In such examples, the emitter 124 may include a housing 140, and the housing 140 may include any of the rails, channels, brackets, clamps, ridges, or other structures of the emitter 124 described above. The housing 140 may comprise a substantially rigid, substantially hollow structure defining an inner space within which one or more optical components, control components, or other components of the system 100 may be located or supported. For instance, the emitter 124 may include one or more light sources 144 disposed within the inner space of the housing 140. The emitter 124 may also include a controller 142 and one or more optics components 146, and in such embodiments, the controller 142 and/or the one or more optics components 146 may be disposed within and/or otherwise connected to the housing 140.

The one or more light sources 144 of the emitter 124 may comprise any component configured to generate one or more beams of light or other radiation. For example, the light source 144 may comprise a light-emitting diode, an incandescent light, a laser, or any other light source. For example, the light source 144 may comprise one or more of a helium-neon gas laser, a laser diode, a diode-pumped solid-state laser, a semiconductor laser, or other laser type. The light source 144 may be configured to generate one or more beams 138a, 138b . . . 138n (where "n" may represent any integer greater than zero) (collectively referred to herein as "beams 138") of visible radiation. For example, such beams 138 may have a wavelength in the visible band (e.g., wavelengths between approximately 600 nm and approximately 400 nm). As such, the beams 138 described herein may comprise relatively narrow (e.g., collimated) coherent beams of visible light configured to form a relatively bright spot or line of colored light when impinging the support surface 126 or any other substantially opaque surface. Such light sources 144 may have a power of less than approximately 5 mW, and may be powered by a power source (e.g., a battery) of the emitter 124, a power source of the vision screening device 104, an external power source (e.g., mains), or any other power source associated with the system 100.

The optics component 146 of the emitter 124 may comprise one or more lenses, windows, prisms, beam splitters, filters, mirrors, and/or any other devices configured to assist in directing the one or more beams 138 of visible radiation generated by the light source 144 to exit the housing 140. For example, the optics component 146 may comprise a collimating lens, a convergent, lens, a divergent lens, and/or any other substantially transparent lens or series of lenses configured to assist in directing such beams 138 to impinge the support surface 126. In such examples, the optics component 146 may receive radiation generated by the light source 144 (e.g., may be disposed optically downstream of the light source 144), and may direct the radiation received from the light source 144 to impinge the support surface 126 at various desired locations along the support surface 126.

For example, one or more lenses, beam splitters, prisms, and/or other structures of the optics component 146 may direct a beam 138a to exit the housing 140 of the emitter 124, and to impinge the support surface 126 at a location A approximately 3 feet or approximately 1 meter from the optics component 146, as measured along the support surface 126. The one or more lenses, beam splitters, prisms, and/or other structures of the optics component 146 may also direct a beam 138b to exit the housing 140 of the emitter 124, and to impinge the support surface 126 at a location B approximately 9 feet or approximately 3 meters from the optics component 146, as measured along the support surface 126. It is understood that the distances described above are merely examples, and in some embodiments, the distances between the emitter 124 and the locations A, B may be greater than or less than those noted above. Further, any of the distances from the emitter 124, the optics component 146, the vision screening device 104 and/or other components of the system 100, to the locations A, B described herein may be measured and/or otherwise determined while the base 122 is disposed on the support surface 126 and the emitter 124, the optics component 146, the vision screening device 104 and/or other components of the system 100 are supported by the base 122.

For example, the optics component 146 may include a substantially transparent window, a lens, a beam splitter, and/or other structure disposed proximate and/or at an outer surface of the housing 140. Such a structure may form an emission face of the optics component 146 and/or of the emitter 124. In such examples, the distance (approximately 3 feet or approximately 1 meter) between the location A on the support surface 126 and the optics component 146 may be measured from a location C on the support surface 126 located substantially vertically beneath the window or other structure of the optics component 146 forming the emission face described above. Likewise, the distance (approximately 9 feet or approximately 1 meter) between the location B on the support surface 126 and the optics component 146 may be measured from the location C.

For example, a central longitudinal axis 136 of the optics component 146 may extend substantially perpendicularly through a center point of the window or other structure of the optics component 146 forming the emission face. The window described above may be disposed in and/or may define a plane extending substantially perpendicular to the axis 136, and the location C on the support surface 126 may comprise a location at which such a plane intersects the support surface 126. In such examples, the location A may be disposed a distance $D_1$ approximately 3 feet or approximately 1 meter from the location C, as measured in a substantially horizontal direction and/or substantially along the support surface 126. Similarly, the location B may be disposed a distance $D_2$ approximately 9 feet or approximately 3 meters from the location C, as measured in a substantially horizontal direction and/or substantially along the support surface 126. As shown in FIG. 1, the optics component 146 may direct the beam 138a at any angle $\Theta_1$ (e.g., an included angle) relative to the axis 136, such that the beam 138a may impinge the support surface 126 at the desired location A. Likewise, the optics component 146 may direct the beam 138b at any angle $\Theta_2$ (e.g., an included angle) relative to the axis 136, such that the beam 138b may impinge the support surface 126 at the desired location B, and in such examples, the angle $\Theta_2$ may be greater than the angle $\Theta_1$.

It is also understood that, in the example illustrated in FIG. 1, the base 122 and/or the mount 128 may be configured such that the emitter 124 is disposed at any desired vertical height $H_1$ relative to and/or from the support surface 126 when the one or more beams 138 impinge the support surface 126 at respective locations. Such a height $H_1$ may be measured substantially vertically from the axis 136 to the support surface 126. In some examples, such as examples in which the one or more legs 123 of the base 122 are extendable in length, the height $H_1$ may comprise a variable height that may be adjusted based on the configuration of the environment in which the system 100 is being used, and/or in order to cause the emitter 124 and/or the optics component 146 to direct the beams 138 of visible radiation to impinge the support surface 126 at desired respective locations from the emitter 124. For instance, increasing the length of the legs 123 (e.g., extending one or more of the legs 123) may cause a commensurate increase in the height $H_1$ at which the emitter 124 is disposed above and/or from the support surface 126. Increasing the length of the legs 123 in this way may also cause a commensurate increase in the distance $D_1$ from the location C to the location A. Increasing the length of the legs 123 in this way may also cause a commensurate increase in the distance $D_2$ from the location C to the location B.

In any of the example systems described herein, such as examples in which one or more legs 123 of the base 122 are extendable in length, one or more of the legs 123 may include a Hall effect sensor, an electrical contact, a switch, a proximity sensor (e.g., an optical sensor), and/or other components configured to form a closed electrical circuit and/or otherwise mate when a desired height $H_1$ is achieved. For example, at least one of the legs 123 may include a first (e.g., upper) portion connected to the mount 128 and a second (e.g., lower) portion moveable relative to (e.g., extendable from and/or retractable relative to) the first portion and configured to contact the support surface 126. In such examples, the first portion of the leg 123 may include a first electrical contact or other electrical component. Additionally, the second portion of the leg 123 may include a second electrical contact or other electrical component moveable with the second portion of the leg 123 relative to the first portion of the leg 123. In such examples, the first electrical contact of the first portion of the leg 123 may mate with (e.g., may complete an electrical circuit with) the second electrical contact of the second portion of the leg 123 when the leg 123 is extended such that the emitter 124 is disposed at the desired vertical height $H_1$ relative to and/or from the support surface 126. The first electrical contact may also be disengaged from (e.g., may form an open circuit) the second electrical contact when the leg 123 is configured such that the emitter 124 is not disposed at the desired vertical height $H_1$ relative to and/or from the support surface 126. The first and second contacts of the leg 123 may be operably connected to the controller 142 and/or to one or more other controllers or processors of the system 100. In such examples, the controller 142 may prohibit the light source 144 from generating the beams 138 until the controller 142 receives a signal or other information from the first electrical contact and/or the second electrical contact indicating that the first electrical contact is mated with the second electrical contact. Put another way, the controller 142 and/or other controllers or processors of the system 100 may be configured to cause the light source 144 to generate one or more of the beams 138 based at least in part on receiving a signal or other information from the first electrical contact and/or the second electrical contact indicating that the first electrical contact is mated with the second electrical contact.

In other examples, such as examples in which the legs 123 of the base 122 are fixed in length, the height $H_1$ may comprise a fixed height (e.g., a fixed vertical height from the support surface 126 to the emitter 124 and/or to the axis 136). In any such examples, the light source 144 of the emitter 124 may generate the beam 138a, and the optics component 146 may direct the beam 138a to impinge the support surface 126 at the location A approximately 3 feet or approximately 1 meter from the emitter 124 (e.g., from the location C) when the base 122 is disposed on the support surface 126 and the emitter 124 is supported by the base 122. Additionally, the light source 144 of the emitter 124 may generate the beam 138b, and the optics component 146 may direct the beam 138b to impinge the support surface 126 at the location B approximately 9 feet or approximately 3 meters from the emitter 124 (e.g., from the location C) when the base 122 is disposed on the support surface 126 and the emitter 124 is supported by the base 122. In examples in which the legs 123 of the base 122 are fixed in length, the emitter 124 may maintain a fixed position relative to the support surface 126 (e.g., a fixed height $H_1$, a fixed angular orientation such that the axis 136 remains substantially parallel to the support surface 126, etc.) when generating and/or emitting the beams 138 described herein.

In any of the examples described herein, the various systems of the present disclosure may further include a distance sensor (e.g., a proximity sensor, or other such sensor). Such a distance sensor may be, for example, connected to the housing 140 of the emitter 124 and/or to the housing 152 of the vision screening device 104. The distance sensor may be configured to determine the distance (e.g., a vertical distance) between the emitter 124 and the support surface 126. In some examples, the distance sensor may be configured to determine the distance between the housing 140 and the support surface 126 and/or the distance between the axis 136 and the support surface 126. In any of the examples described herein, the distance sensor may be operably connected to the controller 142 and/or to one or more other controllers or processors of the system 100. In such examples, the controller 142 may prohibit the light source 144 from generating the beams 138 until the controller 142 receives a signal or other information from the distance sensor indicating that, for example, the emitter 124 is disposed at the desired height $H_1$ from the support surface 126. Put another way, the controller 142 and/or other controllers or processors of the system 100 may be configured to cause the light source 144 to generate one or more of the beams 138 based at least in part on receiving a signal or other information from the distance sensor indicating that the emitter 124 is disposed at the desired height $H_1$ from the support surface 126.

In any of the examples described herein, the controller 142 may also cause one or more displays of the system 100 (e.g., a display of the vision screening device, a display of the emitter 124, etc.) to output information indicative of the measured distance. For instance, if the distance measured by the distance sensor is less than the desired height $H_1$, the controller 142 may cause such a display to provide a message, an image, and/or other information instructing the user 102 to raise the emitter 124 and/or the vision screening device 104 relative to the support surface 126. In such examples, if the distance measured by the distance sensor is greater than the desired height $H_1$, the controller 142 may cause such a display to provide a message, an image, and/or other information instructing the user 102 to lower the emitter 124 and/or the vision screening device 104 relative to the support surface 126. Further, in such examples if the distance measured by the distance sensor is substantially equal to the desired height $H_1$, the controller 142 may cause such a display to provide a message, an image, and/or other information indicating that the emitter 124 and/or the vision screening device 104 is disposed at an acceptable height $H_1$ relative to the support surface 126.

With continued reference to FIG. 1, in some examples the mount 128 may fix the orientation, distance, and/or position of the emitter 124 relative to the base 122 when the housing 140 of the emitter 124 is removably connected to the mount 128. In such examples, the mount 128 may comprise a "fixed" mount. Alternatively, in some examples, the mount 128 may enable the user 102 to modify the orientation, distance, and/or position of the emitter 124 relative to the base 122 when the housing 140 of the emitter 124 is removably connected to the mount 128. For example, the mount 128 may define a substantially central axis 130. In some examples, the axis 130 may extend substantially perpendicular to the axis 136 of the optics component 146 described above, and/or may extend substantially perpendicular to the support surface 126. In any of the examples described herein, the mount 128 may enable, and/or may otherwise be configured to permit rotation of the emitter 124 about the axis 130 when the housing 140 of the emitter 124 is removably connected to the mount 128. For example, the mount 128 may include a first component (e.g., a retainer, a cavity, a joint, a frame/housing having a substantially circular groove, etc.) that remains fixed relative to the base 122 and/or relative to one or more of the legs 123. The mount 128 may also include a second component (e.g., a platform, a bracket, a plate, a rail, etc.) that is rotatable relative to such a first component. The mount 128 may include, for example, one or more fittings, bearings, and/or other structures rotatably coupling the first component to the second component or vice versa. In such examples, the housing 140 of the emitter 124 may be connected to the rotatable second component of the mount 128 such that the emitter 124 may be at least partly rotatable about the axis 130 (e.g., relative to the base 122 and/or relative to the support surface 126) in a clockwise direction 132, and/or in a counterclockwise direction 134. In any of the examples described herein, such an example "fixed" mount 128 may also be configured such that the angles $\Theta_1$, $\Theta_2$ remain fixed during operation of the system 100. Alternatively, in other examples the mount 128 may enable and/or may otherwise be configured to permit rotation of the emitter 124 relative to the support surface 126 so as to change the angles $\Theta_1$, $\Theta_2$ and/or the angular orientation of the emitter 124 relative to the support surface 126.

As noted above, the emitter 124 may also include a controller 142 disposed within the housing 140. In such examples, the controller 142 may be substantially similar to one or more components of the vision screening system 110 described above. For example, the controller 142 may comprise one or more processors, microprocessors, computing devices, and/or other hardware, and/or software components configured to operably control the one or more light sources 144 of the emitter 124. For example, the controller 142 may comprise one or more processors configured to receive various information, signals, and/or other inputs from one or more controls 148 of the emitter 124, from a controller of the vision screening device 104, and/or from the vision screening system 110. In some examples, the one or more controls 148 associated with the emitter 124 may receive inputs from the user 102 during operation of the system 100, and one or more such inputs may comprise a command, or a request for the emitter 124 to generate one or more of the beams 138 described herein.

A control 148 of the emitter 124 may comprise a button, a switch, a trigger, a touchscreen, a keyboard, a microphone, an optical sensor, a video sensor, a camera, and/or other control devices configured to receive touch input, audible commands, visual commands (e.g., hand gestures), and/or other input from the user 102. The control 148 may generate and/or provide corresponding information to the controller 142 based at least in part on receiving such an input from the user 102. In such examples, the controller 142 may be programmed and/or otherwise configured to cause the light source 144 to generate one or more of the beams 138 described herein based at least in part on the input, and/or based at least in part on the information received from the control 148. In any of the examples described herein, the controller 142 may also comprise one or more filters, drivers, amplifiers, and/or other control circuit components configured to assist in controlling the one or more light sources 144 to generate the beams 138 described above. The controller 142 may also be operably connected to any of the power sources described herein, and may be configured to direct current from such power sources to the one or more light sources 144 to assist the light sources 144 in generating the beams 138.

With continued reference to FIG. 1, in any of the examples described herein, the vision screening device 104 may be supported by the base 122. For instance, in some examples the system 100 may further include one or more brackets, rails, joints, fittings, and/or other couplings 150 configured to removably connect a housing 152 of the vision screening device 104 with the housing 140 of the emitter 124. In such examples, the coupling 150 may include one or more first components (e.g., brackets, protrusions, flanges, rails, etc.) connected to, formed by, and/or otherwise extending from the housing 152 of the vision screening device 104. The coupling 150 may also include one or more second components (e.g., brackets, grooves, ridges, slots, holes, etc.) configured to accept, cooperate with, and/or otherwise mate with such first components of the coupling 150 in order to facilitate a removable connection between the housing 152 of the vision screening device 104 and the housing 140 of the emitter 124. In any of the embodiments described herein, such components of the coupling 150 may comprise components of the housing 152 and/or components of the housing 140.

The housing 152 of the vision screening device 104 may be substantially similar to the housing 140 described above with respect to the emitter 124. For example, the housing 152 may comprise a substantially rigid, substantially hollow structure or frame defining an inner space within which one or more display components, control components, sensing components, power supplies, or other components of the system 100 may be located or supported. For instance, the vision screening device 104 may include one or more controllers 154 disposed within the inner space of the housing 152. The vision screening device 104 may further include one or more displays (e.g., a first display 156, a second display 158, etc.) at least partly disposed within and/or supported by the housing 152. The vision screening device 104 may also include various controls 160 operably connected to the controller 154, and/or one or more sensors 162 operably connected to the controller 142. Moreover, as will be described in greater detail below with respect to FIG. 5, an example vision screening device 104 may include one or more additional or alternate components. In any of the examples described herein, the controller 154 and/or other components of the vision screening device 104 may be at least partly disposed within, supported by, and/or otherwise connected to the housing 152.

In some examples, the controller 154 of the vision screening device 104 may be substantially similar to the controller 142 of the emitter 124 and/or substantially similar to one or more components of the vision screening system 110 described above. For example, the controller 154 of the vision screening device 104 may comprise one or more processors and/or other hardware and/or software components configured to operably control the first display 156, the second display 158, the one or more sensor 162, and/or other components of the vision screening device 104. For instance, the controller 154 may include a single processing unit (e.g., a single processor) or a number of processing units (e.g., multiple processors), and can include single or multiple computing units or multiple processing cores. The processor(s) of the controller 154 can be implemented as one or more microprocessors, microcomputers, microcontrollers, digital signal processors, central processing units, state machines, logic circuitries, and/or any devices that manipulate signals based on operational instructions. For example, the processor(s) of the controller 154 can be one or more hardware processors and/or logic circuits of any suitable type specifically programmed or configured to execute the algorithms, operations, and methods described herein. The processor(s) of the controller 154 can be configured to fetch and execute computer-readable instructions stored in the computer-readable media 116, which can program the processor(s) of the controller 154 to perform the functions described herein. Additionally or alternatively, the processor(s) of the controller 154 can be configured to fetch and execute computer-readable instructions stored in computer-readable media and/or other memory of/local to the vision screening device 104.

In any of the examples described herein, the controller 154 may comprise one or more processors configured to receive various information, signals, and/or other inputs from one or more controls 160 of the vision screening device 104. In some examples, the controls 160 may receive such inputs from the user 102 during operation of the system 100, and one or more such inputs may comprise a command or a request for the vision screening device 104 to generate, display, provide, and/or otherwise output one or more Snellen charts, characters, or other images included in a visual acuity examination or other vision test. One or more such inputs may also comprise a command or a request for the vision screening device 104 to generate, display, provide, and/or otherwise output one or more images, beams of radiation, dynamic stimulus, or other output included in a refractive error examination or other vision test. For example, in any of the examples described herein, the controller 154 may be operable to cause the second display 158 to generate, display, provide, and/or otherwise output one or more Snellen charts, characters, or other images included in a visual acuity examination or other vision test. Likewise, the controller 154 may be operable to cause the second display 158 to generate, display, provide, and/or otherwise output one or more images, beams of radiation, dynamic stimulus, or other output included in a refractive error examination or other vision test.

The first display 156 may be disposed on a first side of the housing 152 substantially facing the user 102 during operation of the system 100. The second display 158 may be disposed on a second side of the housing 152 opposite the first side of the housing 152. For example, the second display 158 may be disposed opposite the first display 156, and facing the patient 106 and/or any of the locations A, B described herein. The first display 156 may include a graphical user interface configured to display information to the user 102 and/or receive input from the user 102 during a vision test. For example, the first display 156 may be configured to receive input from the user 102 regarding the patient 106, such as any of the patient information described herein. Further, the first display 156 may be configured to display information regarding the vision screening device 104 (e.g., a current setting or operating mode of the device, etc.), the distance of the patient 106 from the vision screening device 104, the quality of the environment and/or the focus of the vision screening device 104, the progress of the screening, options for transmitting data from the vision screening device 104 to the vision screening system 110, one or more measurements and/or values generated during the vision screening, etc. The first display 156 may comprise, for example, a liquid crystal display (LCD) or active matrix organic light emitting display (AMOLED). The first display 156 may also be touch-sensitive to receive input from the user 102.

Similar to the first display 156, the second display 158 of the vision screening device 104 may comprise, for example, an LCD or an AMOLED. Additionally or alternatively, the second display 158 may include a light-emitting diode (LED) array including one or more visible LEDs and/or one or more near-infrared LEDs. In some examples, a beam splitter included in the vision screening devise 104 may direct light emitted from such an LED array towards the patient 106. The near-infrared LEDs in the LED array may include a wavelength of approximately 850 nanometers (nm) and may be configured to capture video and/or image data associated with the eyes of the patient 106. In some examples, the visible LEDs in the LED array may include a wavelength of less than approximately 630 nm. This allows for a visual stimulus, or graphical representation, to be displayed to the patient 106 without being seen in image/video data captured by the vision screening device 104 (e.g., by an image sensor array of the vision screening device 104, and/or by other sensors or components of the vision screening device 104). In some examples, the visible LEDs may be positioned between, and be substantially co-planar with, the near-infrared LEDs in the LED array.

In some examples, amber LEDs may be among the visible LEDs used in the second display 158. Amber LEDs may include a wavelength of approximately 608 nm to approximately 628 nm. In examples, the amount of power directed to the LEDs in the LED array may be regulated by controller 154 or other components of the vision screening device 104. For example, to minimize the pupil constriction and eye strain of the patient 106, the amber LEDs may be illuminated at low to medium power. For example, a 20 mA LED can be run at between approximately 2 mA to approximately 10 mA. Alternatively, low brightness amber LEDs can be used, for example, such as LEDs that run at about 0.5 mA. Additionally, LEDs can be pulse modulated. Visible light LEDs in colors other than amber, when present in the second display 158, can also be operated at low to medium power.

As noted above, although not shown in FIG. 1 it is understood that in some examples the vision screening device 104 may also include computer-readable media and/or other memory operably connected to the controller 154. In such examples, the controller 154 may be operable to record and/or store details (e.g., results) of the various vision tests performed by the vision screening device 104 in the memory of the vision screening device 104. In any of the examples described herein, the memory of the vision screening device 104 may also store various computer-executable instructions executable by one or more processors of the controller 154. When such instructions are executed by one or more processors of the controller 154, such instructions may cause the controller 154 and/or the one or more processors of the controller 154 to perform any of the methods and/or operations described herein.

The controls 160 may be substantially similar to the control 148 described above with respect to the emitter 124. For example, the one or more controls 160 may comprise a button, a switch, a trigger, a touchscreen, a keyboard, a microphone, an optical sensor, a video sensor, a camera, and/or other control devices configured to receive touch input, audible commands, visual commands (e.g., hand gestures), and/or other input from the user 102. The controls 160 may generate and/or provide corresponding information to the controller 154 based at least in part on receiving such an input from the user 102. In such examples, the controller 154 may be programmed and/or otherwise configured to perform any of the vision test operations described herein based at least in part on the input, and/or based at least in part on the information received from the controls 160. In any of the examples described herein, the controller 142 may also be configured to control operations of the emitter 124 when the vision screening device 104 is operably connected to the emitter 124. In such examples, the controller 154 may communicate with and/or provide instructions to the controller 142 to drive operation of the emitter 124. For instance, in some examples the controller 154 of the vision screening device 104 may be configured to cause the one or more light sources 144 of the emitter 124 to generate one or more of the beams 138 based at least in part on an input received via the one or more controls 160, the first display 156, and/or other components of the vision screening device 104. The controller 154 may receive such input and provide corresponding instructions to the controller 142 of the emitter 124, such that the controller 142 may cause the light sources 144 two omit such beams 138. Alternatively, in such examples, the controller 142 of the emitter 124 may be omitted, and the controller 154 may be configured to directly control operation of the light sources 144.

The one or more sensors 162 may comprise one or more the light sensors configured to detect the ambient light intensity around the vision screening device 204. For example, above certain brightness thresholds, the pupils of the patient 106 may constrict to the point where pupil detection is unreliable or impossible. In this instance, the controller 154, in combination with the one or more light sensors, may determine that the ambient light is too bright and at least one of the first display 156 or the second display 158 may communicate to at least one of the user 102 or the patient 106 to use a light block, to move to an environment with less ambient light, or in some way adjust the screening environment.

Additionally or alternatively, the one or more sensors 162 may comprise one or more proximity sensors configured to determine a distance between the patient 106 and the vision screening device 104. In such examples, the sensor 162 may be configured to determine a distance of the patient 106 from the vision screening device 104. In some examples, the sensor 162 may include an infrared transceiver unit, an ultrasonic transceiver unit, or another distance measuring component known in the art.

Figure 2:
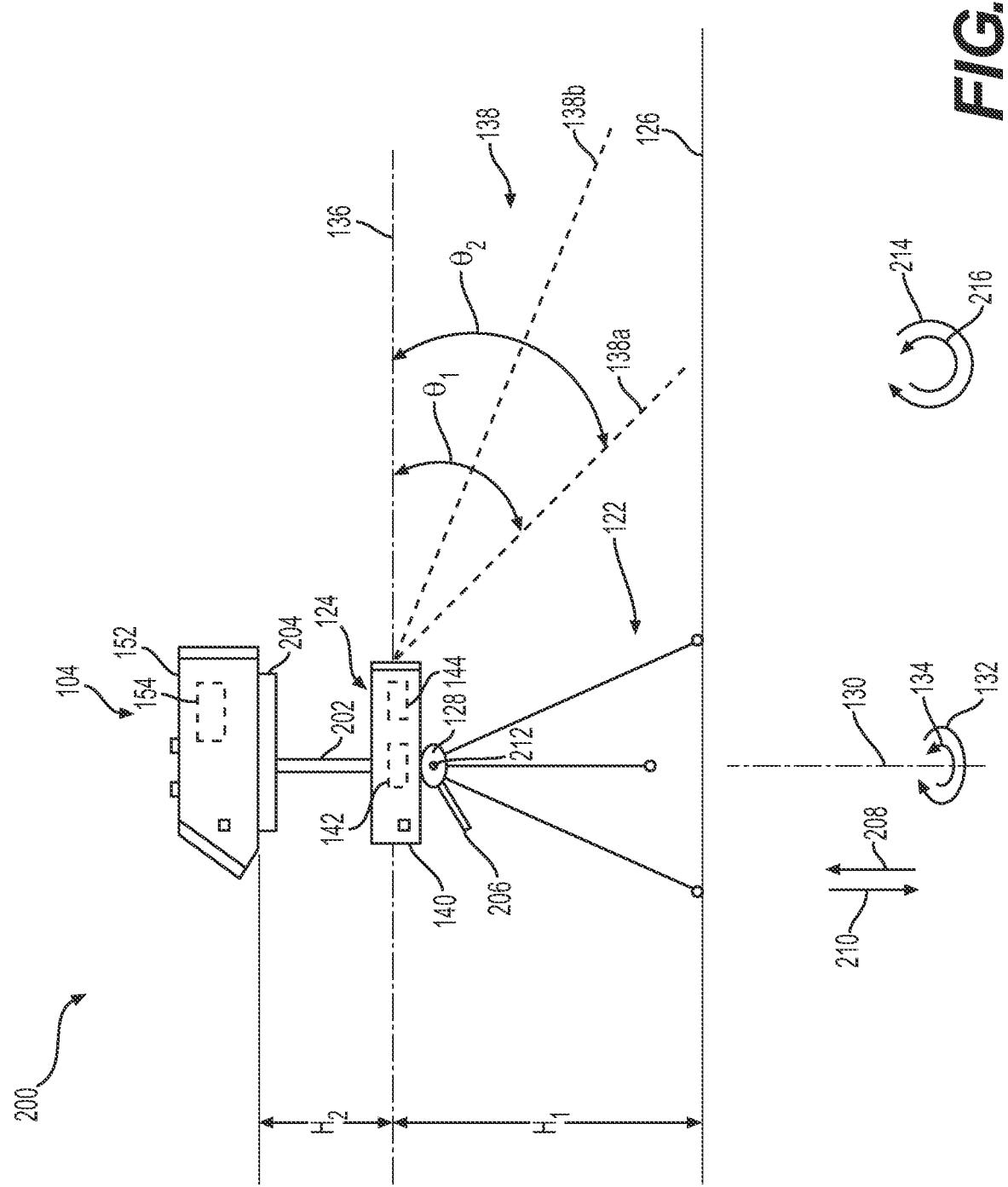
FIG. 2 illustrates another example system of the present disclosure.

FIG. 2 illustrates an additional example system 200 of the present disclosure. As can be seen in FIG. 2, the system 200 may include one or more of the same components included in the system 100, and like components between the systems 100, 200 are illustrated in FIG. 2 using like item numerals. For example, as shown in FIG. 2, the system 200 may include a base 122, and an emitter 124 including one or more light sources 144 operable to generate one or more beams 138 of visible radiation as described above. The system 200 may also include a vision screening device 104 supported by the base 122, and a controller 154 operable to cause a display 158 (FIG. 1) of the vision screening device 104 to output an image included in, for example, the visual acuity examination based at least in part on generation of the one or more visible beams 138. In some examples, such a controller may be a controller 154 of the vision screening device 104. Additionally or alternatively, although not illustrated in FIG. 2, such a controller may comprise one or more processors or controllers of the vision screening system 110 (FIG. 1).

In the example system 200 of FIG. 2, the base 122 may include two or more legs movably connected to a mount 128. As shown in FIG. 2, in some examples the base 122 may comprise a tripod, and the mount 128 may comprise a substantially rigid frame or other housing. The emitter 124 may be removably connected to the mount 128 in any manner. For instance, the mount 128 may include one or more rails, channels, brackets, clamps, or other structures configured to mate with a corresponding rail, channel, bracket, clamp, ridge, or other structure of the emitter 124. In such examples, the emitter 124 may include a housing 140, and the housing 140 may include any of the rails, channels, brackets, clamps, ridges, or other structures of the emitter 124 described above. As described above with respect to FIG. 1, the housing 140 may comprise a substantially rigid, substantially hollow structure defining an inner space within which one or more optical components, control components, or other components may be located or supported.

The system 200 of FIG. 2 may also include a stem 202 movably connected to the mount 128. For example, the stem 202 may comprise a beam, shaft, rod, a bracket, and/or any other substantially rigid structure configured to move in one or more directions relative to the mount 128, and/or relative to the base 122. In some examples, the mount 128 may include one or more grooves, holes, channels, and/or other structures, and in such examples, the stem 202 may be at least partly disposed within and/or movable relative to such structures. The stem 202 may also include a coupling 204 connected to an end of the stem 202, and movable with the stem 202 relative to the mount 128. In such examples, the coupling 204 may be substantially similar to and/or the same as the coupling 150 described above with respect to FIG. 1. For instance, the coupling 204 may comprise one or more platforms, brackets, rails, joints, fittings, and/or other structures configured to removably connect a housing 152 of the vision screening device 104 with the stem 202. The coupling 204 may include one or more components (e.g., flanges, brackets, grooves, ridges, slots, holes, etc.) configured to accept, cooperate with, and/or otherwise mate with one or more corresponding components of the housing 152 in order to facilitate a removable connection between the housing 152 of the vision screening device 104 and the stem 202.

The mount 128 may include one or more handles, levers, knobs, and/or other controls 206 configured to permit movement of the stem 202 relative to the mount 128 and/or to restrict such movement. For example, the control 206 may comprise a releasable locking mechanism configured to permit movement of the stem 202 when the locking mechanism is in a released position, and to prohibit movement of the stem 202 when the locking mechanism is in a locked position. For example, when the locking mechanism or other components of the control 206 is in the released position, the stem 202 and the coupling 204 may be moveable in a substantially vertical direction 208 away from the mount 128 and/or away from the support surface 126, and in a substantially vertical direction 210 toward the mount 128 and/or toward the support surface 126. It is understood that movement of the stem 202, and/or the coupling 204 in the direction 208 away from the support surface 126, while the base 122 is disposed on the support surface 126, may cause commensurate movement of the vision screening device 104 away from the support surface 126. Such commensurate movement of the vision screening device 104 away from the support surface 126 may also comprise movement of the vision screening device 104 in the direction 208 away from the emitter 124. For example, the stem 204 may be movable so as to permit positioning the housing 152 of the vision screening device 104 at any desired distance from the housing 140 of the emitter 124. In some examples the stem 204 may be movable so as to permit positioning the housing 152 of the vision screening device 104 at any desired height $H_2$ relative to the axis 136 described above and/or relative to any other stationary component of the system 200.

It is understood that in any of the examples described herein, an example mount 128 of the present disclosure may facilitate, permit, and/or otherwise enable rotation of one or more components connected thereto relative to the base 122. For example, as described above with respect to FIG. 1, the mount 128 may define a substantially central axis 130 (e.g., a first axis). In some examples, the axis 130 may extend substantially perpendicular to the axis 136 described above, and/or may extend substantially perpendicular to the support surface 126. In any of the examples described herein, the mount 128 may enable, and/or may otherwise be configured to permit rotation of the emitter 124 about the axis 130 when the housing 140 of the emitter 124 is removably connected to the mount 128. As shown in FIG. 2, the mount 128 may also define a substantially central axis 212 (e.g., a second axis) extending substantially perpendicular to the axis 130. In some examples, the axis 212 may also extend substantially perpendicular to the axis 136 described above. In any of the examples described herein, the mount 128 may enable, and/or may otherwise be configured to permit rotation of the emitter 124 about the axis 212 when the housing 140 of the emitter 124 is removably connected to the mount 128. For instance, the mount 128 may enable and/or may otherwise be configured to permit rotation of the emitter 124 about the axis 212 in a clockwise direction 214 and, in a counterclockwise direction 216.

Figure 3:
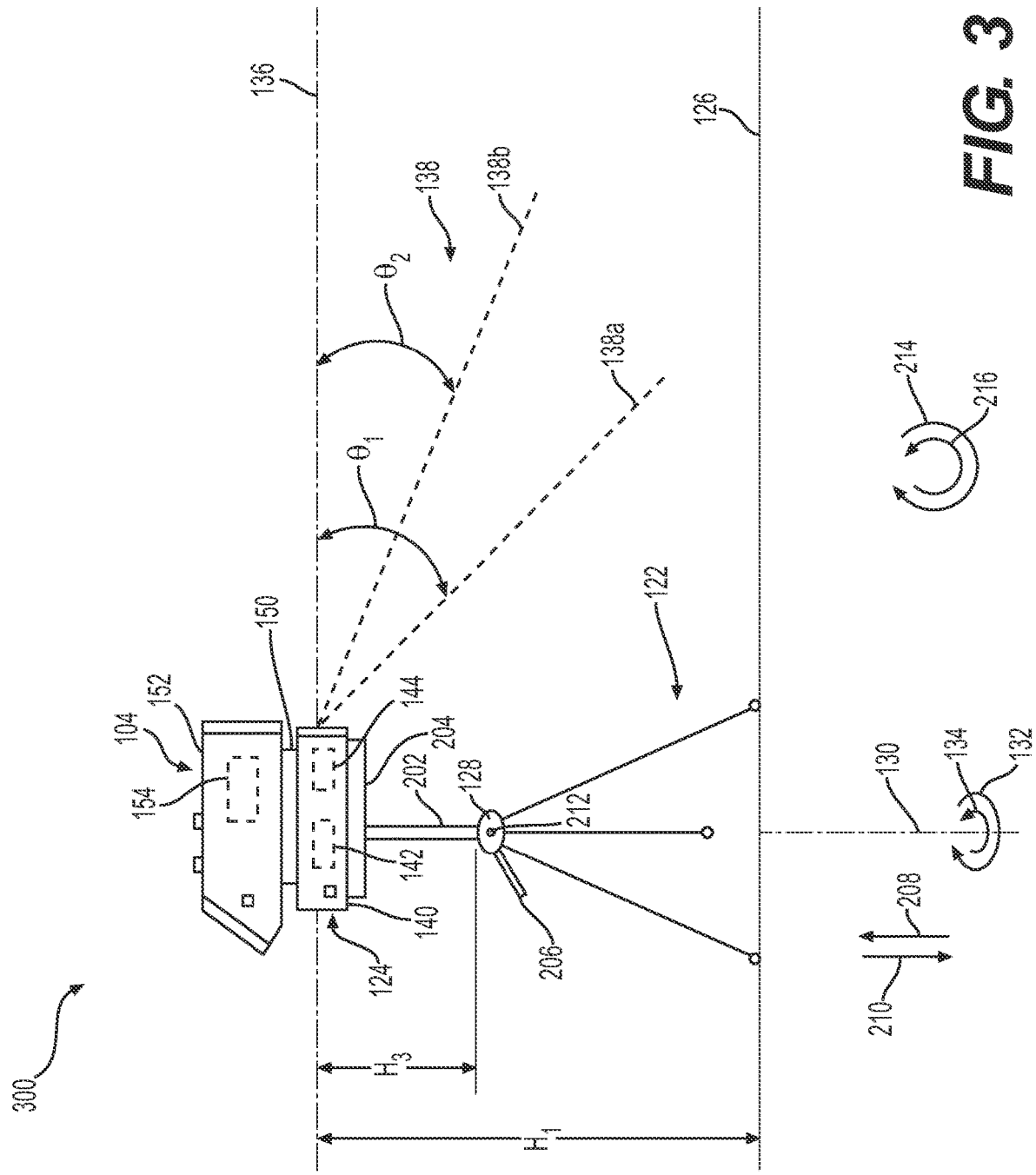
FIG. 3 illustrates still another example system of the present disclosure.

FIG. 3 illustrates another example system 300 of the present disclosure. As can be seen in FIG. 3, the system 300 may include one or more of the same components included in the systems 100, 200, and like components between the systems 100, 200, 300 are illustrated in FIG. 3 using like item numerals. For example, as shown in FIG. 3, the system 300 may include a base 122, and an emitter 124 including one or more light sources 144 operable to generate one or more beams 138 of visible radiation as described above. The system 300 may also include a vision screening device 104 supported by the base 122, and a controller 154 operable to cause a display 158 (FIG. 1) of the vision screening device 104 to output an image included in, for example, the visual acuity examination based at least in part on generation of the one or more visible beams 138. In some examples, such a controller may be a controller 154 of the vision screening device 104. Additionally or alternatively, although not illustrated in FIG. 3, such a controller may comprise one or more processors or controllers of the vision screening system 110 (FIG. 1).

In the example system 300 of FIG. 3, the base 122 may include two or more legs movably connected to a mount 128. The emitter 124 may be removably connected to the mount 128 in any manner. For instance, as shown in FIG. 3, the system 300 may also include a stem 202 movably connected to the mount 128. For example, the stem 202 may comprise a beam, shaft, rod, a bracket, and/or any other substantially rigid structure configured to move in one or more directions relative to the mount 128, and/or relative to the base 122. In some examples, the mount 128 may include one or more grooves, holes, channels, and/or other structures, and in such examples, the stem 202 may be at least partly disposed within and/or movable relative to such structures.

As described with respect to FIG. 2, the stem 202 may also include a coupling 204 connected to an end of the stem 202, and movable with the stem 202 relative to the mount 128. In such examples, the coupling 204 may be substantially similar to and/or the same as the coupling 150 described above with respect to FIG. 1. For instance, the coupling 204 may comprise one or more platforms, brackets, rails, joints, fittings, and/or other structures configured to removably connect a housing 140 of the emitter with the stem 202. The coupling 204 may include one or more components (e.g., flanges, brackets, grooves, ridges, slots, holes, etc.) configured to accept, cooperate with, and/or otherwise mate with one or more corresponding components of the housing 140 in order to facilitate a removable connection between the housing 140 of the emitter 124 and the stem 202.

The mount 128 may include one or more handles, levers, knobs, and/or other controls 206 configured to permit movement of the stem 202 relative to the mount 128 and/or to restrict such movement. For example, as described above with respect to FIG. 2, the control 206 may comprise a releasable locking mechanism configured to permit movement of the stem 202 when the locking mechanism is in a released position, and to prohibit movement of the stem 202 when the locking mechanism is in a locked position. For example, when the locking mechanism or other components of the control 206 is in the released position, the stem 202 and the coupling 204 may be moveable in a substantially vertical direction 208 away from the mount 128 and/or away from the support surface 126, and in a substantially vertical direction 210 toward the mount 128 and/or toward the support surface 126. It is understood that movement of the stem 202, and/or the coupling 204 in the direction 208 away from the support surface 126, while the base 122 is disposed on the support surface 126, may cause commensurate movement of the emitter 124 and the vision screening device 104 away from the support surface 126. For example, the stem 204 shown in FIG. 3 may be movable so as to permit positioning the housing 140 of the emitter 124 at any desired distance from the mount 128. In some examples the stem 204 may be movable so as to permit positioning the housing 140 of the emitter 124 at any desired height $H_3$ relative to the mount 128 and/or relative to any other stationary component of the system 300. Further, the mount 128 shown in FIG. 3 may be configured to enable rotation of the stem 202, and any components connected thereto, about the axis 130 and/or about the axis 212.

Similar to the one or more extendable legs 123 described above with respect to FIG. 1, in some examples the mount 128 shown in FIG. 3 may include a first electrical contact or other electrical component. Additionally, the stem 202 shown in FIG. 3 may include a second electrical contact or other electrical component moveable with the stem 202 relative to the mount 128. In such examples, the first electrical contact of the mount 128 may mate with (e.g., may complete an electrical circuit with) the second electrical contact of the stem 202 when the stem 202 is extended such that the emitter 124 is disposed at the desired vertical height $H_1$ relative to and/or from the support surface 126. In such examples, the first electrical contact of the mount 128 may also mate with the second electrical contact of the stem 202 when the stem 202 is extended such that the emitter 124 is disposed at the desired vertical height $H_3$ relative to and/or from the mount 128. The controller 142 and/or other controllers or processors of the system 300 may be configured to cause the light source 144 to generate one or more of the beams 138 based at least in part on receiving a signal or other information from the first electrical contact and/or the second electrical contact indicating that the first electrical contact is mated with the second electrical contact.

In the example system 300 of FIG. 3, the housing 140 of the emitter 124 may be separate from the housing 152 of the vision screening device 104. Similar to FIG. 1, the system 300 may further include one or more brackets, rails, joints, fittings, and/or other couplings 150 configured to removably connect the housing 152 of the vision screening device 104 with the housing 140 of the emitter 124. As noted with respect to FIG. 1, the coupling 150 may include one or more first components (e.g., brackets, protrusions, flanges, rails, etc.) connected to, formed by, and/or otherwise extending from the housing 152 of the vision screening device 104. The coupling 150 may also include one or more second components (e.g., brackets, grooves, ridges, slots, holes, etc.) configured to accept, cooperate with, and/or otherwise mate with such first components of the coupling 150 in order to facilitate a removable connection between the housing 152 of the vision screening device 104 and the housing 140 of the emitter 124. In any of the embodiments described herein, such components of the coupling 150 may comprise components of the housing 152 and/or components of the housing 140.

Figure 4:
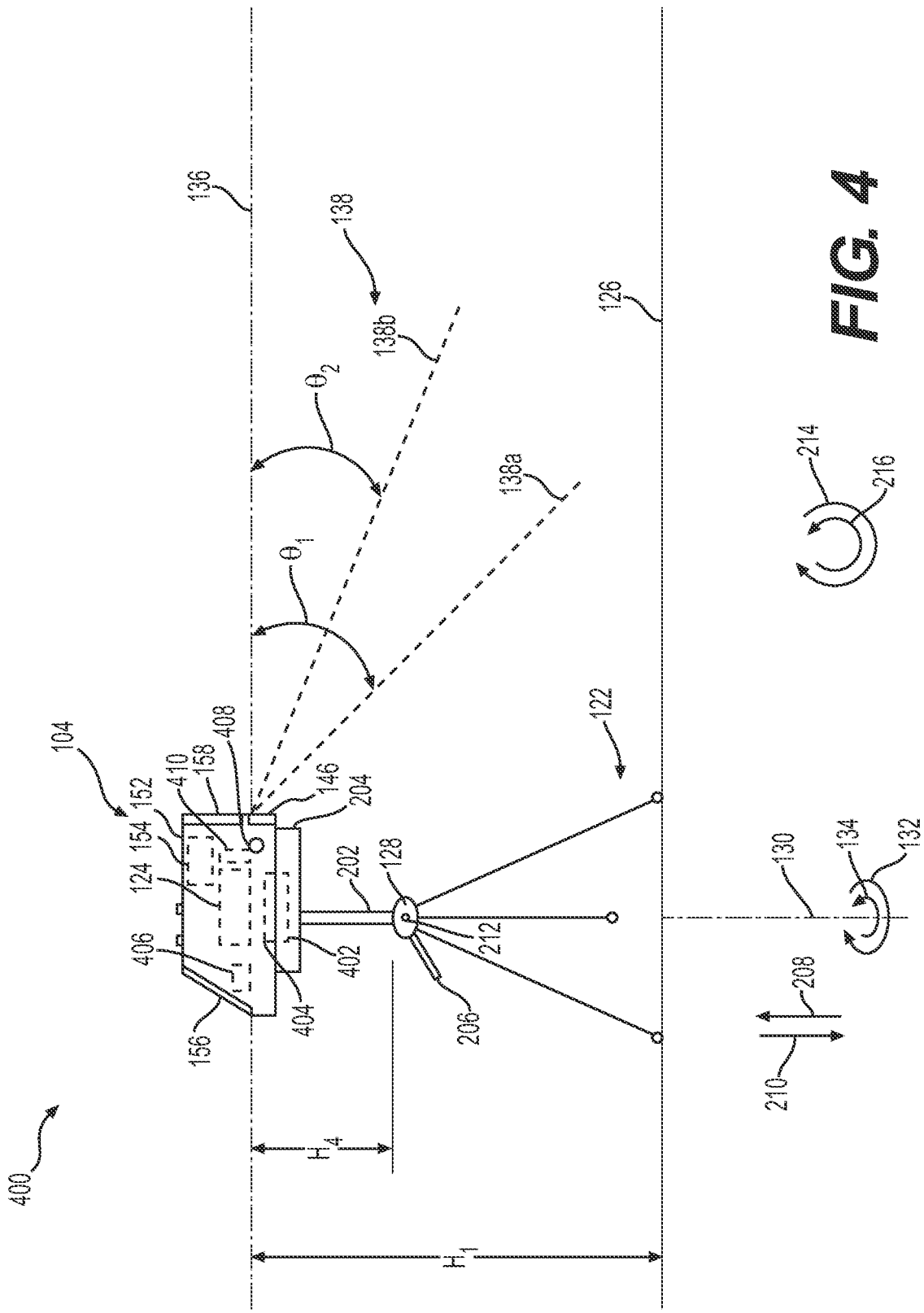
FIG. 4 illustrates yet another example system of the present disclosure. Similar to FIG. 1, in some implementations, components of the example systems shown in FIGS. 2-4 may be used to perform one or more tests associated with vision screening.

FIG. 4 illustrates yet another example system 400 of the present disclosure. As can be seen in FIG. 4, the system 400 may include one or more of the same components included in the systems 100, 200, 300, and like components between the systems 100, 200, 300, 400 are illustrated in FIG. 4 using like item numerals. For example, as shown in FIG. 4, the system 400 may include a base 122, and an emitter 124 including one or more light sources operable to generate one or more beams 138 of visible radiation as described above. The system 400 may also include a vision screening device 104 supported by the base 122, and a controller 154 operable to cause a display 158 (FIG. 1) of the vision screening device 104 to output an image included in, for example, the visual acuity examination based at least in part on generation of the one or more visible beams 138. In some examples, such a controller may be a controller 154 of the vision screening device 104. Additionally or alternatively, although not illustrated in FIG. 4, such a controller may comprise one or more processors or controllers of the vision screening system 110 (FIG. 1).

In the example system 400 of FIG. 4, the base 122 may include two or more legs movably connected to a mount 128. Further, in the system 400 the vision screening device 104 may comprise a housing 152 defining an interior space. In such examples, the emitter 124 may be disposed within the interior space of the housing 152. For example, the emitter 124 may include one or more light sources 410 configured to generate one or more of the beams 138 described herein. In such examples, the one or more light sources 410 of the emitter 124 may be disposed within the housing 152 of the vision screening device 104.

The example light source 410 shown in FIG. 4 may be substantially similar to and/or the same as the light sources 144 described above with respect to at least FIG. 1. For example, the light source 410 may comprise one or more of a helium-neon gas laser, a laser diode, a diode-pumped solid-state laser, a semiconductor laser, or other laser type. The light source 410 may be configured to generate one or more beams 138 of visible radiation having a wavelength in the visible band (e.g., wavelengths between approximately 600 nm and approximately 400 nm). The beams 138 generated by the light source 410 may comprise relatively narrow (e.g., collimated) coherent beams of visible light configured to form a relatively bright spot or line of colored light when impinging the support surface 126 or any other substantially opaque surface. The light source 410 may have a power of less than approximately 5 mW, and may be powered by a power source (e.g., a battery) of the vision screening device 104, an external power source (e.g., mains), or any other power source associated with the system 400.

The system 400 may also include an optics component 146 disposed at least partly within, carried by, and/or otherwise connected to the housing 152. The optics component 146 may be substantially similar to the optics component 146 described above with respect to FIG. 1. For instance, the optics component 146 shown in FIG. 4 may comprise one or more lenses, windows, prisms, beam splitters, filters, mirrors, and/or any other devices configured to assist in directing the one or more beams 138 of visible radiation generated by the light source 410 to exit the housing 152 of the vision screening device 104. For example, the optics component 146 may comprise a collimating lens, a convergent, lens, a divergent lens, and/or any other substantially transparent lens or series of lenses configured to assist in directing such beams 138 to impinge the support surface 126. In such examples, the optics component 146 may receive radiation generated by the light source 410 (e.g., may be disposed optically downstream of the light source 410), and may direct the radiation received from the light source 410 to impinge the support surface 126 at various desired locations (e.g., locations A, B described above) along the support surface 126.

The housing 152 of the vision screening device 104 shown in FIG. 4 may be removably connected to the mount 128 and/or to the base 122 in any manner. For instance, as shown in FIG. 4, the system 400 may also include a stem 202 movably connected to the mount 128 and/or to the base 122. For example, the stem 202 may comprise a beam, shaft, rod, a bracket, and/or any other substantially rigid structure configured to move in one or more directions 208, 210 relative to the mount 128, and/or relative to the base 122. In some examples, the mount 128 may include one or more grooves, holes, channels, and/or other structures, and in such examples, the stem 202 may be at least partly disposed within and/or movable relative to such structures.

As described with respect to FIG. 2, the stem 202 of the system 400 may also include a coupling 204 connected to an end of the stem 202, and movable with the stem 202 relative to the mount 128. In such examples, the coupling 204 may be substantially similar to and/or the same as the coupling 150 described above with respect to FIG. 1. For instance, the coupling 204 of the system 400 may comprise one or more platforms, brackets, rails, joints, fittings, and/or other structures configured to removably connect the housing 152 of the vision screening device 104 with the stem 202. The coupling 204 may include one or more components (e.g., flanges, brackets, grooves, ridges, slots, holes, etc.) configured to accept, cooperate with, and/or otherwise mate with one or more corresponding components of the housing 152 in order to facilitate a removable connection between the housing 152 of the vision screening device 104 and the stem 202.

The mount 128 may include one or more handles, levers, knobs, and/or other controls 206 configured to permit movement of the stem 202 relative to the mount 128 and/or to restrict such movement. For example, as described above with respect to FIG. 2, the control 206 may comprise a releasable locking mechanism configured to permit movement of the stem 202 when the locking mechanism is in a released position, and to prohibit movement of the stem 202 when the locking mechanism is in a locked position.

It is understood that movement of the stem 202 and/or the coupling 204 in the direction 208 away from the support surface 126, while the base 122 is disposed on the support surface 126, may cause commensurate movement of the vision screening device 104 of the system 400 away from the support surface 126. For example, the stem 204 shown in FIG. 4 may be movable so as to permit positioning the housing 152 of the vision screening device 104 at any desired distance from the mount 128. In some examples the stem 204 may be movable so as to permit positioning the housing 152 of the vision screening device 104 at any desired height $H_4$ relative to the mount 128 and/or relative to any other stationary component of the system 400. Further, the mount 128 shown in FIG. 4 may be configured to enable rotation of the stem 202, and any components connected thereto, about the axis 130 and/or about the axis 212.

Similar to the one or more extendable legs 123 described above with respect to FIG. 1, in some examples the mount 128 shown in FIG. 4 may include a first electrical contact or other electrical component. Additionally, the stem 202 shown in FIG. 4 may include a second electrical contact or other electrical component moveable with the stem 202 relative to the mount 128. In such examples, the first electrical contact of the mount 128 may mate with (e.g., may complete an electrical circuit with) the second electrical contact of the stem 202 when the stem 202 is extended such that the vision screening device 104 is disposed at the desired vertical height $H_1$ relative to and/or from the support surface 126. In such examples, the first electrical contact of the mount 128 may also mate with the second electrical contact of the stem 202 when the stem 202 is extended such that the vision screening device 104 is disposed at the desired vertical height $H_4$ relative to and/or from the mount 128. The controller 154 of the vision screening device 104 and/or other controllers or processors of the system 400 may be configured to cause the light source 410 to generate one or more of the beams 138 based at least in part on receiving a signal or other information from the first electrical contact and/or the second electrical contact indicating that the first electrical contact is mated with the second electrical contact.

It is understood that any of the example systems described herein may include one or more electrical connectors, sensors, or other electrical components configured to enable a controller of the system to determine whether a vision screening device 104 from an approved manufacturer has been connected thereto. For example, as shown in FIG. 4, the system 400 may include a coupling 204 having a first electrical connector 402. In such examples, the housing 152 of the vision screening device 104 may include a second electrical connector 404 configured to mate with the first electrical connector 402 when the housing 152 is removably connected to the stem 202. In such examples, the first electrical connector 402 may include one or more female connection components such as one or more ports, jacks, magnetic readers, RFID readers, near field communication readers, barcode scanners, and/or other components. Similarly, the second electrical connector 404 may include one or more male connection components configured to mate with the female connection components of the first electrical connector 402. Such male connection components may include, for example, one or more pins, prongs, magnetic couplings, RFID tags, near field communication, tags, barcodes, and/or other components. While the first electrical connector 402 has been described herein as including one or more female connection components and the second electrical connector 404 has been described herein as including one or more male components, in additional examples, the first electrical connector 402 may include one or more male components and the second electrical connector 404 may include one or more female components.

In such examples, the controller 154 of the vision screening device 104 may be operably connected to the first electrical connector 402, and/or the second electrical connector 404. For example, removably connecting the housing 152 of the vision screening device 104 to the coupling 204 may include mechanically connecting and/or electrically connecting the second electrical connector 404 with the first electrical connector 402. In such examples, mechanically or electrically connecting the second electrical connector 404 with the first electrical connector 402 may operably connect the controller 154 of the vision screening device 104 (and/or a controller of the vision screening system 110) with the first electrical connector 402, and/or the second electrical connector.

In examples in which, as described above, the first electrical connector 402 comprises one or more female connection components such as one or more ports, jacks, magnetic readers, RFID readers, near field communication readers, barcode scanners, and/or other components configured to mate with the second electrical connector 404, one or more such components of the first electrical connector 402 may be configured to generate and/or provide one or more signals, and/or other information to the controller 154 (and/or a controller of the vision screening system 110) when the second electrical connector 404 is mated with the first electrical connector 402. For example, the first electrical connector 402 may provide information to the controller 154 indicating that a mechanical and/or electrical connection between the first electrical connector 402 and the second electrical connector 404 has been made. The first electrical connector 402 may read, sense, determine, collect, and/or otherwise receive such information from the second electrical connector 404 and/or other components of the vision screening device 104. Such information may include, for example, one or more part numbers, security codes, identification keys, and/or other identifiers uniquely identifying the vision screening device 104. The controller 154 and/or the controller of the vision screening system 110 may be configured to determine whether such information includes, among other things, one or more valid connection parameters associated with the vision screening device 104. For example, the controller 154 and/or the controller of the vision screening system 110 may compare such information with additional information included in memory associated with the vision screening device 104, the computer readable media 116, the database 120, and/or other components of the system 100.

In such examples, the controller 154 and/or the controller of the vision screening system 110 may determine whether the information received from the first electrical connector 402 matches additional information stored in memory and indicative of one or more acceptable vision screening devices. For example, the computer readable media 116, the database 120, and/or other components of the system 100 may include one or more lists identifying acceptable vision screen devices, acceptable vision screening device manufacturers, and/or other information identifying components or devices that are acceptable for use with the base 122 and/or with the system 400. In examples in which the controller 154 and/or the controller of the vision screening system 110 determine that the unique identifier, information, and/or other connection parameters received from the first electrical connector 402 is not included in and/or otherwise does not match information stored in the computer readable media 116, the database 120, and/or other components of the system 100, the controller 154 and/or the controller of the vision screening system 110 may provide a signal and/or other indication indicating that the vision screen device 104 is not acceptable for use with the system 400. In some examples, such an indication may be provided to the vision screening device 104 via the network 108. In such examples, the controller 154 of the vision screening device 104 may cause the first display 156 and/or the second display 158 of the vision screen device 104 to display and/or otherwise output information indicating that the vision screen device 104 is not acceptable for use with the system 400. Additionally or alternatively, the controller 154 may prohibit use of the vision screen device 104 for one or more vision tests based at least in part on receiving such an indication.

On the other hand, in examples in which the controller 154 and/or the controller of the vision screening system 110 determine that the unique identifier, information, and/or other connection parameters received from the first electrical connector 402 is included in and/or otherwise does match information stored in the computer readable media 116, the database 120, and/or other components of the system 100, the controller 154 and/or the controller of the vision screening system 110 may provide (e.g., via the network 108) a signal and/or other indication indicating that the vision screen device 104 is acceptable for use with the system 400. In some examples, the controller 154 of the vision screening device 104 may cause the first display 156 and/or the second display 158 of the vision screen device 104 to display and/or otherwise output information indicating that the vision screen device 104 is acceptable for use with the system 400. Additionally or alternatively, the controller 154 may enable use of the vision screen device 104 for one or more vision tests based at least in part on receiving such an indication. For instance, in any of the examples described herein, the controller 154 may be programmed, configured, and/or otherwise operable to cause the one or more light sources 144 of the emitter 124 to generate one or more of the beams 138 described herein based at least in part on such an indication (e.g., based at least in part on the second electrical connector 404 mating with the first electrical connector 402).

With continued reference to FIG. 4, the vison screening device 104 may further include one or more sensors 406, such as one or more the light sensors configured to detect the ambient light intensity around the vision screening device 104. Additionally or alternatively, the one or more sensors 406 may comprise one or more proximity sensors configured to determine a distance between the patient 106 and the vision screening device 104. Such sensors 406 may be operably connected to the controller 154 of the vision screening device 104, and may be substantially similar to and/or the same as the one or more sensors 162 described above with respect to FIG. 1. Moreover, in any of the example systems described herein, the vision screening device 104 may include one or more accelerometers, gyroscopes, and/or sensors 406 operably connected to the controller 154 of the vision screening device 104. Such sensors 406 may be configured to sense, detect, and/or otherwise determine motion and/or orientation of the vision screening device 104. As illustrated in the example system 400 of FIG. 4, one or more such accelerometers, gyroscopes, and/or other sensors 406 may be disposed within, supported by, and/or otherwise connected to the housing 152 of the vision screening device 104.

Moreover, in addition to the one or more controls 160 described above, in examples in which the vision screening device 104 includes one or more light sources 410 and/or other components of the emitter 124 disposed within the housing 152, the vision screening device 104 may further include one or more controls operably connected to such components and configured to control operation of such components. For example, as shown in FIG. 4, the vision screening device 104 may include one or more controls 408 configured to receive input associated with and/or otherwise control operational aspects of the emitter 124. In some examples, the control 408 may receive such inputs from the user 102 during operation of the system 400, and one or more such inputs may comprise a command, or a request for the emitter 124 to generate one or more of the beams 138 described herein. Similar to the control 148 described above with respect to at least FIG. 1, the one or more controls 408 may comprise a button, a switch, a trigger, a touchscreen, a keyboard, a microphone, an optical sensor, a video sensor, a camera, and/or other control devices configured to receive touch input, audible commands, visual commands (e.g., hand gestures), and/or other input from the user 102. The control 408 may generate and/or provide corresponding information to the controller 154 of the vision screening device 104 based at least in part on receiving such an input from the user 102. In such examples, the controller 154 may be programmed and/or otherwise configured to cause the light source 410 to generate one or more of the beams 138 described herein based at least in part on the input, and/or based at least in part on the information received from the control 408.

Figure 5:
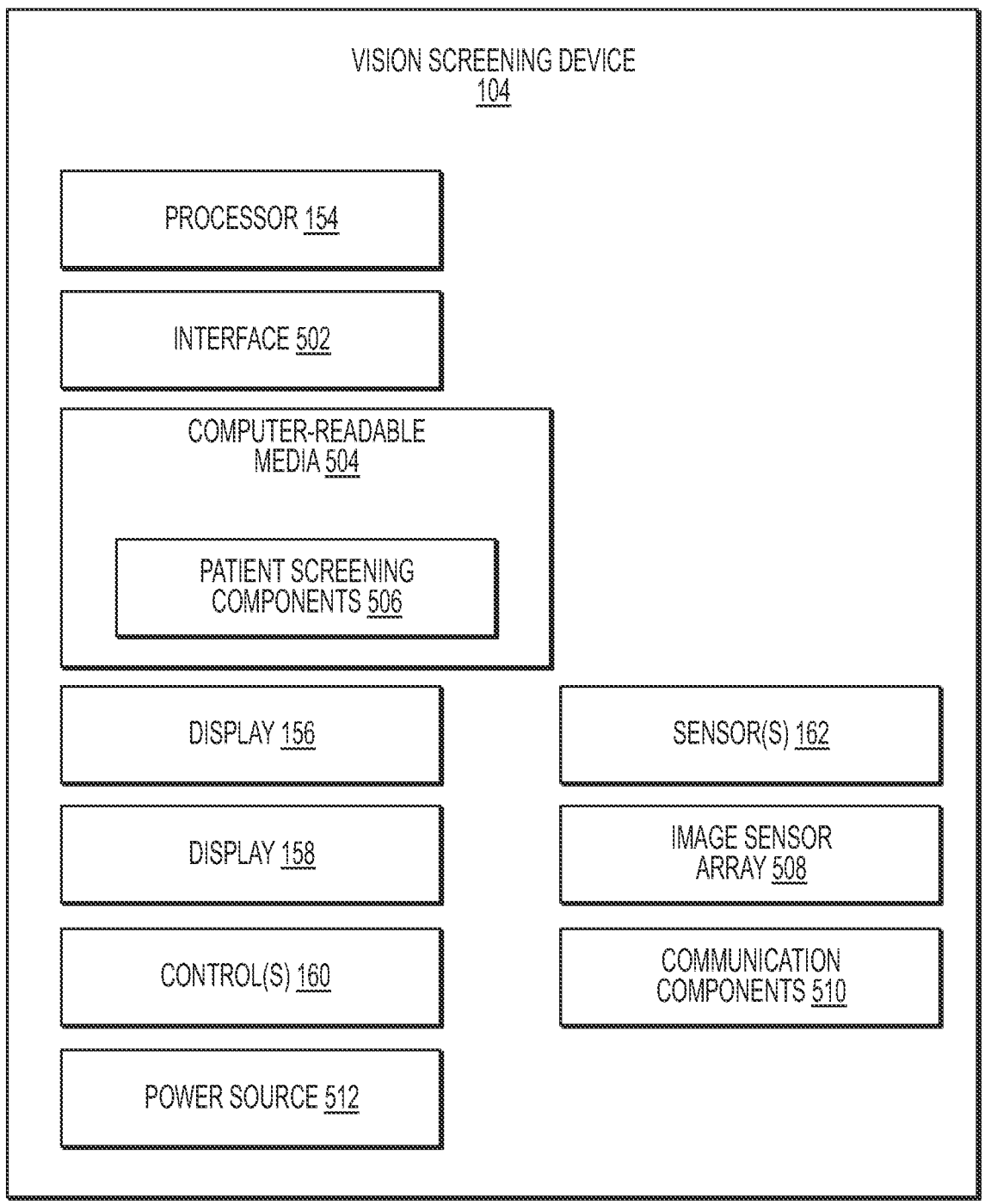
FIG. 5 provides a schematic illustration of an example vision screening device of the present disclosure.

FIG. 5 provides a schematic illustration of an example vision screening device 104 of the present disclosure. It is understood that any of the components described above with respect to the vision screening devices 104 of FIGS. 1-4 may be included in the example vision screening device 104 shown schematically in FIG. 5 regardless of whether such components are expressly illustrated in FIG. 5. Additionally, like components between the systems 100, 200, 300, 400 are illustrated in FIG. 5 using like item numerals. For example, as shown in FIG. 5, the vision screening device 104 may include one or more processors 154 and/or other controller components. In some examples, the processors 154 shown schematically in FIG. 5 may comprise one or more of the controllers 154 described above with respect to FIGS. 1-4. The vision screening device 104 may also include a first display 156, a second display 158, and one or more controls 160. In some examples, such controls 160 may include one or more of the controls 408 described above with respect to FIG. 4. The vision screening device 104 shown in FIG. 5 may also include one or more sensors 162, and in some examples, one or more of the sensors 162 may include an accelerometer, a gyroscope, and/or any of the other sensors 406 described above with respect to FIG. 4. Moreover, as will be described in greater detail below, an example vision screening device 104 may include computer-readable media 504 containing various patient screening components 506. An example vision screening device 104 may also include an image sensor array 508, one or more communication components 510, and/or a power source 512.

In the example shown in FIG. 5, the processor 154 of the vision screening device 104 may comprise one or more controllers, processors, and/or other hardware and/or software components configured to operably control the first display 156, the second display 158, the one or more sensor 162, the image sensor array 508, the communication components 510, the emitter 124 (not shown), the one or more light sources 144, 410 (not shown), and/or other components of the vision screening device 104. For instance, the processor 154 shown in FIG. 5 may include a single processing unit (e.g., a single processor) or a number of processing units (e.g., multiple processors), and can include single or multiple computing units or multiple processing cores. The processor 154 shown in FIG. 5 can be implemented as one or more microprocessors, microcomputers, microcontrollers, digital signal processors, central processing units, state machines, logic circuitries, and/or any devices that manipulate signals based on operational instructions. For example, processor 154 shown in FIG. 5 can be one or more hardware processors and/or logic circuits of any suitable type specifically programmed or configured to execute the algorithms, operations, and methods described herein. The processor 154 shown in FIG. 5 can be configured to fetch and execute computer-readable instructions stored in the computer-readable media 504, which can program the processor 154 to perform the functions described herein. Additionally or alternatively, the processor 154 shown in FIG. 5 can be configured to fetch and execute computer-readable instructions stored in computer-readable media 116 of the vision screening system 110 (FIG. 1).

In any of the examples described herein, the processor 154 shown in FIG. 5 may be configured to receive various information, signals, and/or other inputs from one or more of the controls 160, the sensors 162, the display 156, the display 158, the image sensor array 508, and/or other components of the vision screening device 104. In some examples, the controls 160 may receive such inputs from the user 102, and one or more such inputs may comprise a command or a request for the vision screening device 104 to generate, display, provide, and/or otherwise output one or more Snellen charts, characters, or other images included in a visual acuity examination or other vision test. One or more such inputs may also comprise a command or a request for the vision screening device 104 to generate, display, provide, and/or otherwise output one or more images, beams of radiation, dynamic stimulus, or other output included in a refractive error examination or other vision test. For example, the processor 154 shown in FIG. 5 may be operable to cause the second display 158 to generate, display, provide, and/or otherwise output one or more Snellen charts, characters, or other images included in a visual acuity examination or other vision test. Likewise, the processor 154 shown in FIG. 5 may be operable to cause the second display 158 to generate, display, provide, and/or otherwise output one or more images, beams of radiation, dynamic stimulus, or other output included in a refractive error examination or other vision test.

In some respects, the computer-readable media 504 shown in FIG. 5 may be similar to the computer-readable media 116 described above with respect to the vision screening system 110 (FIG. 1). For example, the computer-readable media 504 may include volatile and nonvolatile memory and/or removable and non-removable media implemented in any type of technology for storage of information, such as computer-readable instructions, data structures, program modules, or other data. Such computer-readable media 504 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 504 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 504 can be used to store any number of functional components that are executable by the processor(s) 154. In many implementations, these functional components comprise instructions or programs that are executable by the processor(s) 154 and that, when executed, specifically configure the one or more processor(s) 154 to perform the actions described herein and associated with one or more vision screening tests.

The interface(s) 502 of the vision screening device 104 shown in FIG. 5 may enable wired and/or wireless communications between the vision screening device 104 and one or more components of the vision screening system 110 (FIG. 1), as well as with one or more other remote systems and/or other networked devices. For instance, the interface 502 may include a personal area network component to enable communications over one or more short-range wireless communication channels. Furthermore, the interface 502 may include a wide area network component to enable communication over a wide area network. In any of the examples described herein, the interface 502 may enable communication between the vision screening device 104 and the vision screening system 110 via the network 108 (FIG. 1).

With continued reference to FIG. 5, the computer-readable media 504 may include any number of functional components that are executable by the processor(s) 154. In many implementations, these components comprise instructions or programs that are executable by the processor(s) 154 and that, when executed, specifically configure the one or more processors 154 to perform the actions attributed to the vision screening device 104. For example, as described herein, the patient screening components 506 may be configured to receive, access, store, and/or analyze various data associated with the patient 106 in order to determine patient data for use by the vision screening device 104. For example, the patient screening components 506 may be configured to receive/access patient data indicating demographic information associated with the patient 106. For instance, the patient screening components 506 may be configured to receive patient data entered by the user 102 and indicating the age, ethnicity, gender, name, address, and/or other characteristics of the patient 106 (e.g., patient provided or determined otherwise), as well as a desired vision test to be performed. In examples, the patient screening components 506 may also be configured to receive/access patient data from a database (e.g., the database 120) associated with the vision screening system 110. Still further, in examples, the patient screening components 506 may be configured to receive/access image/video data from the image/video sensor array component 508 of the vision screening device 104 and/or any other information from the sensors 162. The patient screening components 506 may be configured to analyze any such information to determine certain characteristics associated with the patient 106, such as visual acuity, refractive error, etc.

Other functional components stored in the computer-readable media 504 may include, among other things, a graphical representation data component, a measurement data component, a threshold data component, a notification component, a sensor data component, a range finder data component, a microphone data component, a light source control component, a machine learning component, and/or any other functional component associated with the operation of the vision screening device 104.

For instance, in some examples the computer-readable media 504 may include a graphical representation data component. The graphical representation data component may be configured to determine and/or generate one or more graphical representations for display to the patient 106 during a vision test. For example, the graphical representation data component may be configured to receive and/or access patient data from the patient screening component 506 to determine a characteristic and/or testing category associated with the patient 106 (e.g., toddler, senior, nearsighted, etc.). Utilizing this information, the graphical representation data component may determine a type of graphical representation to generate for display to the patient 106. For example, if the patient data indicates that the patient 106 is being screened for dynamic pupil tracking, the vision screening device 104 may generate a moving image for display to the patient 106 in order to track how the pupil movement of the patient 106 during the screening.

In examples, the computer-readable media 504 may also include a measurement data component. For example, the measurement data component may be configured to receive/access image/video data from the image/video sensor array 508 of the vision screening device 104. The measurement data component may also be configured to receive/access sensor data received from any of the sensors 162, 406 described herein. The measurement data component may further be configured to analyze such received data to determine one or more measurements associated with the patient 106 throughout the vision test. For example, the measurement data component may be configured to analyze the image/video data to determine a location of the patient's pupils and/or lenses, a diameter of the pupils and/or lenses (e.g., indicating expansion or contraction), a motion of the pupils and/or lenses (e.g., indicating a convergence or divergence), a gaze of the patient, etc. from the data. The measurement data component may also be configured to analyze data received from the sensors 162, 406 described herein to determine the visual acuity of the patient 106 and/or the refractive error of the patient 106. The measurements may be determined as at points in time while the graphical representation is being displayed. In examples, the measurement data component may be configured to determine one or more measurements associated with the patient 106 during the screening. For example, the measurement data component may be configured to determine the visual acuity, the refractive error, the position of one or both of the patient's pupils, and/or other results of the vision test being performed by the vision screening device 104. In some examples, the measurement data component may be configured to analyze the image/video data described herein to determine such results.

For example, the measurement data component may be configured to receive/access image/video data from the image/video sensor array 508 of the vision screening device 104 to determine a gaze direction of the patient in response to being displayed the graphical representation. For example, the gaze of the patient 106 may be determined by shining a light, such as an infrared light, in the direction of the patient 106. In response, the cornea of the patient 106 may reflect the light and the reflection may be included, or visible, in the image or video data. The measurement data component may utilize the reflection to determine a glint, or straight-line measurement, from the source of the light to the center of the eye (e.g., the origin of the reflection). As such, the measurement data component may utilize this information to determine a position, location, and/or motion of the pupil at different points in time while the graphical representation is being displayed. In other examples, the measurement data component may utilize the image/video data to determine the position or location of the pupil may be determined relative to the outside edges of the eye (e.g., the outline of the eye). The measurement data component may utilize the measurements associated with the gaze of the patient to determine one or more locations of the patient's pupils at points in time while being displayed the graphical representation (e.g., position vs. time data points).

In examples, the computer-readable media 504 may also include a threshold data component. The threshold data component may be configured to receive, access, and/or analyze threshold data associated with standard testing results. For example, the threshold data component may be configured to access, or receive data from, a third-party database storing testing data and/or measurements, or a range of values indicating a threshold within which testing values should lie, associated with patients having normal vision health with similar testing conditions. For example, for each testing category, standard testing data may be accessed or received by the threshold data component and may be utilized for comparison against the measurement data stored by the measurement data component.

Alternatively, or in addition, the threshold data component may be configured to utilize one or more machine learning techniques to determine threshold data associated with each testing category and/or graphical representation. For example, the threshold data component may be configured to utilize one or more algorithms and/or trained machine learning models to determine threshold data. For example, the threshold data component may execute one or more algorithms (e.g., decision trees, artificial neural networks, association rule learning, or any other machine learning algorithm) to determine the one or more threshold values based on historical vision screening data. In response, the threshold data component may be configured to utilize the trained models to determine one or more threshold values and/or standard values for use by the vision screening device 104.

In examples, the computer-readable media 504 may also include a notification component. For example, the notification component may be configured to receive and/or access the results of the various vision tests from the measurement data component, and provide an indication of the results to the user 102 conducting the vision test. For instance, the notification component may be configured to output such results via at least one of the first display 156 and/or the second display 158. The notification component may also be configured to provide such results to the vision screening system 110 via the network 108.

In further examples, the computer-readable media 504 may include a microphone component. The microphone component may be configured to receive responses spoken by patient 106 and generate audio data associated with the responses. For example, the patient 106 may provide auditory responses as part of the visual acuity test and/or other vision tests described herein. For example, the patient 106 may be asked to read an optotype, such as a letter, shown on the second display 158 and the microphone component may be configured to receive the patient's responses. In response, the microphone component may be configured to generate audio data associated the responses and/or provide the audio data to the processor 154 shown in FIG. 5. In combination with voice recognition software, the microphone component and/or other functional components of the computer-readable media 504 may decode the responses to generate audio data, and may use the audio data in the various vision tests described herein.

With continued reference to FIG. 5, the image/video sensor array 508 of the vision screening device 104 may be configured to receive and/or access light, image, and/or video data associated with a patient 106 being evaluated during a vision test. In particular, the image/video sensor array 508 may be configured to capture, or generate, image and/or video data during the vision test. For example, as described herein, image data and/or video data may be generated by the image/video sensor array 508 during a vision screening to determine initial patient data, one or more measurements associated with the body and eyes of the patient 106, and the like. In some examples, the image/video data may be transmitted, via the interface(s) 502, to the vision screening system 110 for processing and analysis.

In some examples, the image/video sensor array 508 includes, for example, a complementary metal-oxide semiconductor (CMOS) sensor array, also known as an active pixel sensor (APS), or a charge connected device (CCD) sensor. In some examples, a lens is supported by the vision screening device 104 and positioned in front of the image/video sensor array 508. In still further examples, the image/video sensor array 508 has a plurality of rows of pixels and a plurality of columns of pixels. For example, the image/video sensor array 508 may include approximately 1280 by 1024 pixels, approximately 640 by 480 pixels, approximately 1500 by 1152 pixels, approximately 2048 by 1536 pixels, and/or approximately 2560 by 1920 pixels. The image/video sensor array component 212 may be capable of capturing approximately 25 frames per second (fps), approximately 30 fps, approximately 35 fps, approximately 40 fps, approximately 50 fps, approximately 75 fps, approximately 100 fps, approximately 150 fps, approximately 200 fps, approximately 225 fps, and/or approximately 250 fps.

Note that the above pixel values and frames per second are exemplary, and other values may be greater or less than the examples described herein.

In examples, the image/video sensor array 508 may include photodiodes having a light-receiving surface and have substantially uniform length and width. During exposure, the photodiodes convert the incident light to a charge. The image/video sensor array 508 may be operated as a global shutter. For example, substantially all of the photodiodes may be exposed simultaneously and for substantially identical lengths of time. Alternatively, the image/video sensor array 508 may be used with a rolling shutter mechanism, in which exposures move as a wave from one side of an image to the other. Other mechanisms are possible to operate the image/video sensor array 508 in yet other examples. The image/video sensor array 508 may also be configured to capture digital images. The digital images can be captured in various formats, such as JPEG, BITMAP, TIFF, etc.

The communication components 510 of the example vision screening device 104 shown in FIG. 5 may be configured to connect to external databases (e.g., the database 120) to receive, access, and/or send screening data using wireless connections. Wireless connections can include cellular network connections and connections made using protocols such as 802.11a, b, g, and/or ac. In other examples, a wireless connection can be accomplished directly between the vision screening device 104 and an external display using one or more wired or wireless protocols, such as Bluetooth, Wi-Fi Direct, radio-frequency identification (RFID), or Zigbee. Other configurations are possible. The communication of data to an external database can enable report printing or further assessment of the patient's visual test data. For example, data collected and corresponding test results may be wirelessly transmitted and stored in a remote database accessible by authorized medical professionals.

Further, it is understood that the power source 512 may comprise any removable, rechargeable, and/or other power source known in the art and configured to store electrical power. The power source 512 may comprise one or more rechargeable batteries configured to selectively provide electrical current to the one or more components of the vision screening device 104 during use. For instance, the power source 512 may comprise one or more sealed lead acid batteries, lithium ion batteries, nickel cadmium batteries, nickel-metal hydride batteries, or other types of batteries configured to provide sufficient power to the first display 156, the second display 158, the one or more processors 154, the image sensor array 508, and/or other components of the visions screening device 104 during multiple vision tests.

Figure 6:
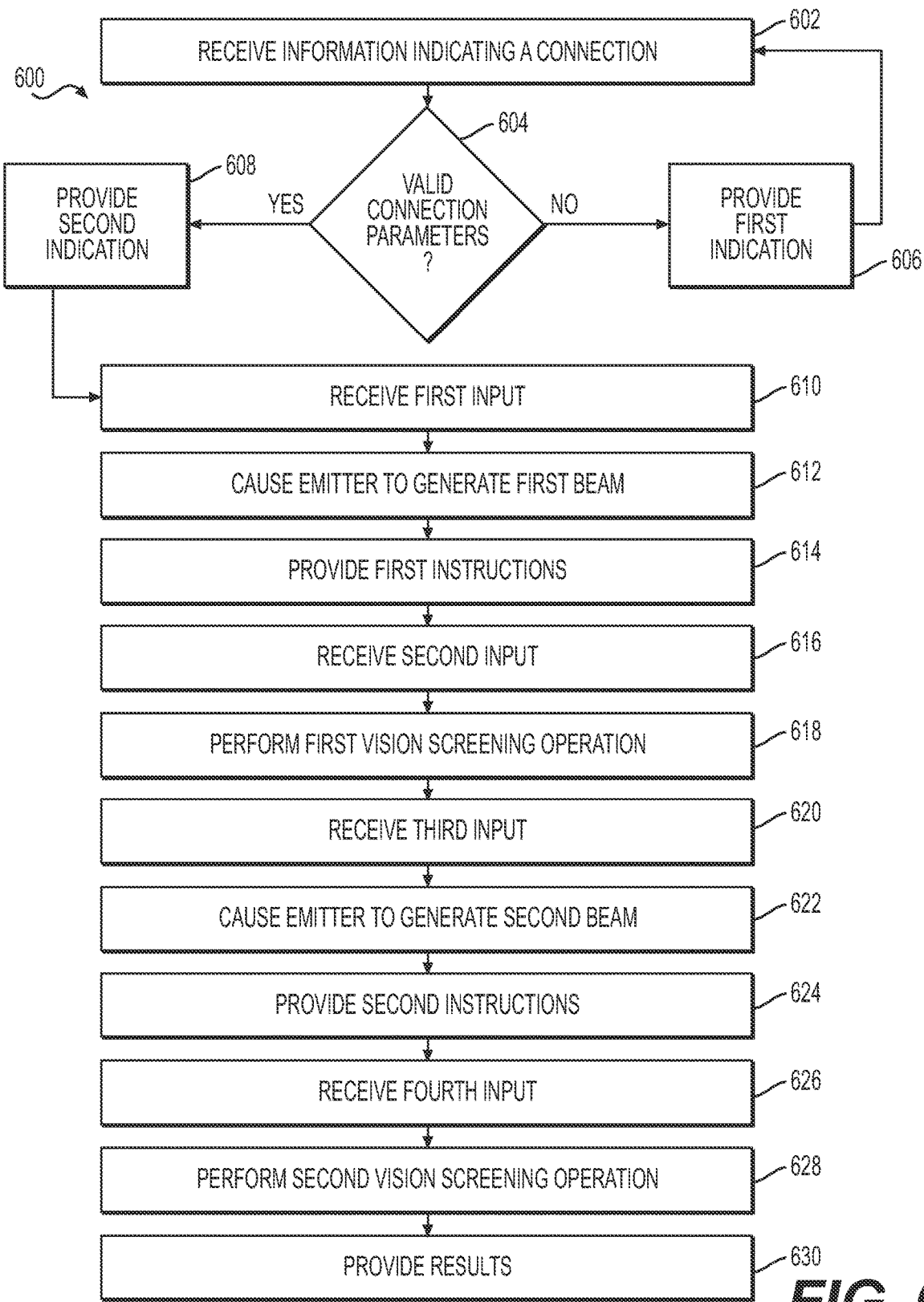
FIG. 6 provides a flow diagram illustrating an example method of the present disclosure.

FIG. 6 provides a flow diagram illustrating an example method 600 for vision testing, as described herein. The method 600 is illustrated as collections of blocks in a logical flow graph, which represents a sequence of operations that can be implemented in hardware, software, or a combination thereof. In the context of software, the blocks represent computer-executable instructions stored on one or more computer-readable storage media that, when executed by processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the method 600. In some embodiments, one or more blocks of the method 600 can be omitted entirely.

The operations described below with respect to the method 600 can be performed by any of the systems 100, 200, 300, 400 described herein, and/or by various components thereof. Unless otherwise specified, and for ease of description, the method 600 will be described below with reference to the system 100 shown in FIG. 1. In particular, although any of the operations described with respect to the method 600 may be performed by the controller 154 of the vision screening device 104, the controller 142 of the emitter, the one or more processors 114 of the vision screening system 110, and/or other components of the system 100, either alone or in combination, the method 600 will be described below with respect to the system 100 and/or the controller 154 unless otherwise specified.

At 602, the controller 154 and/or one or more processors associated therewith may receive information indicating that at least one of a mechanical or electrical connection has been made between a first electrical connector 402 (FIG. 4) of the coupling 204 and a second electrical connector 404 associated with the housing 152 of the vision screening device 104. For example, removably connecting the housing 152 of the vision screening device 104 to the coupling 204 may include mechanically connecting and/or electrically connecting the second electrical connector 404 with the first electrical connector 402.

For example, at 602 the first electrical connector 402 may provide information to the controller 154 indicating that a mechanical and/or electrical connection between the first electrical connector 402 and the second electrical connector 404 has been made. The first electrical connector 402 may read, sense, determine, collect, and/or otherwise receive such information from the second electrical connector 404 and/or other components of the vision screening device 104. Such information may include, for example, one or more part numbers, security codes, identification keys, and/or other identifiers uniquely identifying the vision screening device 104.

At 604, the controller 154 and/or the controller of the vision screening system 110 may determine whether the information received at 602 includes, among other things, one or more valid connection parameters associated with the vision screening device 104. For example, at 604 the controller 154 may compare such received information with additional information included in memory associated with the vision screening device 104, the computer readable media 116, the database 120, and/or other components of the system 100. In such examples, the controller 154 may determine, at 604, whether the information received at 602 matches additional information stored in memory and indicative of one or more acceptable vision screening devices 104. For example, the computer readable media 116, the database 120, and/or other components of the system 100 may include one or more lists identifying acceptable vision screen devices, acceptable vision screening device manufacturers, and/or other information identifying components or devices that are acceptable for use with the base 122 and/or with the various systems described herein.

In examples in which the controller 154 determines that the unique identifier, information, and/or other connection parameters received at 602 is not included in and/or otherwise does not match information stored in the computer readable media 116, the database 120, and/or other components of the system 100 (604—No), at 606 the controller 154 may provide a signal and/or other indication indicating that the vision screen device 104 is not acceptable for use with the system 400. In some examples, at 606 the controller 154 may provide such an indication by causing the first display 156 and/or the second display 158 of the vision screen device 104 to display and/or otherwise output information indicating that the vision screen device 104 is not acceptable for use with the system 100. Additionally or alternatively, the controller 154 may prohibit use of the vision screen device 104 for one or more vision tests based at least in part on the determination made at 604.

In other examples, at 606, the controller 154 may provide an option to proceed with one or more vision screening tests even though the unique identifier, information, and/or other connection parameters received at 602 is not included in and/or otherwise does not match information stored in the computer readable media 116, the database 120, and/or other components of the system 100. In such examples, at or after 606, the controller 154 may provide, via the first display 156, a user interface including an input field enabling the user 102 to indicate whether the user 102 wishes to continue using the current vision screening device 104 and/or the current base 122. If the controller 154 receives an input from the user 102 (e.g., via the user interface and/or via one or more of the controls 160) indicating that the user 102 does wish to continue using the current vision screening device 104 and/or the current base 122, the controller 154 may cause the first display 156 to display and/or otherwise output one or more additional user interfaces enabling the user 102 to perform vision screening tests manually or otherwise using the vision screen device 104. In some such examples, the controller 154 may proceed to step 610 based at least in part on receiving such an input from the user 102. Alternatively, in such examples, if the controller 154 receives an input from the user 102 indicating that the user 102 does not wish to continue using the current vision screening device 104 and/or the current base 122, the controller 154 may return to step 602.

In examples in which the controller 154 determines that the unique identifier, information, and/or other connection parameters received at 602 is included in and/or otherwise does match information stored in the computer readable media 116, the database 120, and/or other components of the system 100 (604—Yes), at 608 the controller 154 may provide a signal and/or other indication indicating that the vision screen device 104 is acceptable for use with the system 100. In some examples, at 608 the controller 154 may provide such an indication by causing the first display 156 and/or the second display 158 of the vision screen device 104 to display and/or otherwise output information indicating that the vision screen device 104 is acceptable for use with the system 100. Additionally or alternatively, the controller 154 may enable use of the vision screen device 104 for one or more vision tests based at least in part on the determination made at 604. For instance, in any of the examples described herein, the controller 154 may be programmed, configured, and/or otherwise operable to cause the one or more light sources 144 of the emitter 124 to generate one or more of the beams 138 described herein based at least in part on the determination made at 604.

At 610, the controller 154 may receive a first input from the user 102. In such examples, the input received at 610 may comprise, among other things, a request from the user 102 for the emitter 124 to generate one or more beams 138 of visible radiation. In such examples, the user 102 may provide such an input using one or more touch commands entered via the first display 156. Additionally or alternatively, the user 102 may provide such an input via one or more controls 160 of the vision screen device 104. In still further examples, at 610 the user 102 may provide such an input via one or more controls 148 of the emitter 124. In any of the examples described herein, the first input received at 610 may comprise a request for the one or more light sources 144 of the emitter 124 to generate the beam 138a of visible radiation impinging the substantially horizontal support surface 126 at the location A, a distance $D_1$ approximately one meter from the emitter 124 when the base 122 is disposed on the support surface 126 and the emitter 124 is supported by the base 122.

At 612, the controller 154 may cause the emitter 124 to generate the beam 138a. For example, at 612 the controller 154 may cause a power source operably connected to the emitter 124 to provide electrical current to the light source 144 and/or other components of the emitter 124, thereby causing the light source 144 to generate the beam 138a.

At 614, the controller 154 may generate and/or otherwise provide first instructions to the user 102. For example, based at least in part on the input received at 610, at 614 the controller 154 may generate first instructions requesting that the patient 106 be positioned at the location A on the support surface 126. In such examples, at 614 the controller 154 may cause the first display 156 to display and/or otherwise output the instructions such that the user 102 may read and/or otherwise consume the instructions, and verbalize a corresponding request to the patient 106. Additionally or alternatively, at 614 the controller 154 may cause the second display 158 to display, and/or otherwise output the instructions such that the patient 106 may read and/or otherwise consume the instructions directly.

At 616, the controller 154 may receive a second input from the user 102. In such examples, the input received at 616 may comprise, among other things, a confirmation from the user 102 that the patient 106 is currently disposed at a location A on the support surface 126. In such examples, the user 102 may provide such an input using one or more touch commands entered via the first display 156. Additionally or alternatively, the user 102 may provide such an input via one or more controls 160 of the vision screen device 104. In still further examples, at 616 the user 102 may provide such an input via one or more controls 148 of the emitter 124. In any of the examples described herein, the input received at 616 may comprise an indication that the patient 106 is standing at, proximate, and/or just marginally behind the location A visibly identified by the beam 138a. As described above, positioning the patient 106 at the location A may be desirable for one or more vision tests including, for example, a refractive error test.

At 618, the controller 154 may perform a first vision screening operation and/or other portion of a vision test on the patient 106. For example, based at least in part on receiving the second input at 616, the controller 154 may output one or more images, visual stimuli, and/or other outputs via the second display 158. For example, during a refractive error test, at 618 the controller 154 may cause the second display 158 to display, output, and/or otherwise provide different focused and blurred (e.g., fogged) images to the patient 106. Such blurred images or other such fogged stimuli may cause the patient's eye to relax. At 618, the controller 154 may also cause the image sensor array 508, the second display 158, and/or other components of the vision screening device 104 to capture a series of refractive error measurements during this process. In particular, at 618 the controller 154 may cause the image sensor array 508 to capture refractive error measurements while the various focused and blurred images are presented to the patient 106 via the second display 158. In some examples, the measurements will have large variations in value due to some measurements corresponding to a pre-accommodation condition of the patient's eye lens, and other measurements corresponding to a post accommodation condition of the patient's eye lens. At 618, the patient screening components 506 and/or other components stored in the computer-readable media 504 may use one or more algorithms, machine learning techniques, neural networks, look-up tables and/or other components to analyze the refractive error measurement data in order to determine, for example, a refractive error associated with each eye of the patient 106.

In some such examples, at 618 the controller 154 may cause the second display 158 to display, output, and/or otherwise provide a stimulus that may cause the patient 106 to gaze near and far to send the eye into two states. At 618 the controller 154 may also cause the image sensor array 508 to capture a series of refractive error measurements during this process. In particular, the controller 154 may cause the image sensor array 508 to capture refractive error measurements while the eye of the patient 106 is in each of the respective states, and while the eye transitions between the two states. The patient screening components 506 and/or other components stored in the computer-readable media 504 may use one or more algorithms, machine learning techniques, neural networks, look-up tables and/or other components to analyze such refractive error measurement data to more accurately determine, for example, the refractive error of the patient 106.

At 620, the controller 154 may receive a third input from the user 102. In such examples, the input received at 620 may comprise, among other things, a request from the user 102 for the emitter 124 to generate one or more additional beams 138 of visible radiation. In such examples, at 620 the user 102 may provide such an input using one or more touch commands entered via the first display 156, via one or more controls 160 of the vision screen device 104, and/or via one or more controls 148 of the emitter 124. In any of the examples described herein, the third input received at 620 may comprise a request for the one or more light sources 144 of the emitter 124 to generate the beam 138b of visible radiation impinging the substantially horizontal support surface 126 at the location B, a distance $D_2$ approximately three meters from the emitter 124 when the base 122 is disposed on the support surface 126 and the emitter 124 is supported by the base 122.

At 622, the controller 154 may cause the emitter 124 to generate the beam 138b. For example, at 620 the controller 154 may cause a power source operably connected to the emitter 124 to provide electrical current to the light source 144 and/or other components of the emitter 124, thereby causing the light source 144 to generate the beam 138b.

At 624, the controller 154 may generate and/or otherwise provide second instructions to the user 102. For example, based at least in part on the input received at 620, at 624 the controller 154 may generate second instructions requesting that the patient 106 be positioned at the location B on the support surface 126. In such examples, at 624 the controller 154 may cause the first display 156 to display and/or otherwise output the instructions such that the user 102 may read and/or otherwise consume the instructions, and verbalize a corresponding request to the patient 106. Additionally or alternatively, at 624 the controller 154 may cause the second display 158 to display, and/or otherwise output the instructions such that the patient 106 may read and/or otherwise consume the instructions directly.

At 626, the controller 154 may receive a fourth input from the user 102. In such examples, the fourth input received at 626 may comprise, among other things, a confirmation from the user 102 that the patient 106 is currently disposed at a location B on the support surface 126. In such examples, at 626 the user 102 may provide such an input using one or more touch commands entered via the first display 156, via one or more controls 160 of the vision screen device 104, and/or via one or more controls 148 of the emitter 124. In any of the examples described herein, the fourth input received at 626 may comprise an indication that the patient 106 is standing at, proximate, and/or just marginally behind the location B visibly identified by the beam 138b. As described above, positioning the patient 106 at the location B may be desirable for one or more vision tests including, for example, a visual acuity test.

At 628, the controller 154 may perform a second vision screening operation and/or other portion of a vision test on the patient 106. For example, based at least in part on receiving the fourth input at 626, at 628 the controller 154 may output one or more images, characters, visual stimuli, and/or other outputs via the second display 158. For example, during a visual acuity test, at 628 the controller 154 may cause the second display 158 to display, output, and/or otherwise provide at least part (e.g., one or more rows) of a Snellen chart. In some examples, at 628 the controller 154 may cause the second display 158 to display one or more characters, optotypes, or other Snellen equivalent figures. Additionally or alternatively, at 628 the controller 154 may cause the second display 158 to flash an optotype to the patient 106 so that the patient 106 can confirm a target Snellen equivalent. In some examples, at 628 the controller 154 may control the vision screening device 104 to perform such visual acuity tests in different dedicated operating modes that are tuned based on the age of the patient (e.g., a "child" mode, an "adult" mode, a "geriatric" mode, or other testing category) and/or based on the skill of the user 102 (e.g., an "optometrist" mode, a "streamlined" mode, etc.).

In any such examples, at 628 the controller 154 may cause the image sensor array 508 to capture various visual acuity measurements during this process. In particular, at 628 the controller 154 may cause the image sensor array 508 to capture measurements of the patient's eye while the patient 106 is viewing the displayed optotypes. Additionally or alternatively, at 628 the controller 154 may receive one or more inputs entered by the user 102 and indicative of the patient's response to the optotypes displayed via the second display 158. The controller 154 may employ any of the patient screening components 506 to determine the visual acuity of the patient 106 based at least in part on the inputs received at 628.

At 630, the controller 154 may cause the first display 156 and/or the second display 158 to display, output, and/or otherwise provide the one or more refractive error values determined at 618 and/or the results of the visual acuity test determined at 628. Additionally or alternatively, at 630 the controller 154 may provide the one or more refractive error values and/or the results of the visual acuity test to the vision screening system 110 via the network 108.

Based at least on the description herein, it is understood that the systems and methods of the present disclosure may be used to assist in performing one or more visual acuity tests, refractive error tests, or other vision tests. For example, components of the systems described herein may be configured to generate respective beams of visible radiation, and to direct such beams to impinge a support surface. Such beams may, thus, form a visible spot, line, or other indication on the support surface to identify locations at which a patient should be disposed during the respective tests. As a result, the systems described herein may assist a user with properly positioning the patient at different locations particular to the respective vision test being performed, thereby improving the accuracy of each test and streamlining the workflow for physicians, nurse practitioners, and other users.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A system, comprising:
   a base;
   a mount supported by the base;
   a housing supported by the base;
   an emitter including a light source operable to generate a beam of visible radiation, the beam of radiation impinging a substantially horizontal support surface at a location approximately three meters from the emitter when the base is disposed on the support surface and the emitter is supported by the base,
   wherein the base and the mount are configured to maintain the emitter at a fixed vertical height from the support surface when the beam impinges the support surface at the location;
   a vision screening device supported by the base, the vision screening device having a first display, and a second display opposite the first display and facing the location; and
   a controller operable to cause the second display to output an image included in a visual acuity examination based at least in part on generation of the visible beam.

2. The system of claim 1, wherein the emitter and the light source are disposed within the housing, and the housing is removably connected to the base via the mount.

3. The system of claim 2, wherein the emitter includes an optics component directing the beam to exit the housing, the beam impinging the support surface at the location approximately three meters from the optics component as measured along the support surface.

4. The system of claim 2, wherein the housing comprises a first housing, the vision screening device including a second housing removably connected to the first housing.

5. The system of claim 2, wherein the mount enables rotation of the emitter about a first axis extending substantially perpendicular to the support surface, and about a second axis extending substantially perpendicular to the first axis.

6. The system of claim 2, further comprising a stem movably connected to the mount, the vision screening device being removably connected to the stem such that the movement of the stem in a direction away from the support surface while the base is disposed on the support surface causes commensurate movement of the vision screening device away from the support surface.

7. The system of claim 6, wherein the commensurate movement of the vision screening device comprises movement of the vision screening device in the direction and away from the emitter.

8. The system of claim 1, wherein the emitter and the light source are disposed within the housing, the system further comprising a stem moveably connected to the base via a mount,
   the emitter being removably connected to the stem such that movement of the stem in a direction away from the support surface while the bases is disposed on the support surface causes commensurate movement of the emitter and the vision screening device away from the support surface.

9. The system of claim 8, wherein the housing comprises a first housing, the vision screening device including a second housing removably connected to the first housing.

10. The system of claim 1, wherein the vision screening device and the light source are disposed within the housing.

11. The system of claim 10, further comprising at least one of an accelerometer and a gyroscope disposed within the housing.

12. The system of claim 10, further comprising a stem movably connected to the base, wherein:
   the housing is removably connected to the stem via a coupling,
   the coupling includes a first electrical connector, and
   the housing includes a second electrical connector configured to mate with the first electrical connector when the housing is removably connected to the stem.

13. The system of claim 12, wherein the controller is operable to cause the light source to generate the beam based at least in part on the second electrical connector mating with the first electrical connector.

14. The system of claim 1, wherein the controller comprises a controller of the vision screening device, and the controller is configured to cause the light source to generate the beam based at least in part on an input received via the vision screening device.

15. The system of claim 1, wherein the beam comprises a first beam, the location comprises a first location, and the light source is operable to generate a second beam of visible radiation,
   the second beam impinging the support surface at a second location approximately one meter from the emitter when the base is disposed on the support surface and the emitter is supported by the base,
   the emitter maintaining a fixed position relative to the support surface when emitting the first beam and the second beam.

16. A system, comprising:
   memory;
   one or more processors; and
   computer-executable instructions stored in the memory and executable by the one or more processors to perform operations comprising:
      causing a light source of an emitter to generate a beam of visible radiation,
      the light source being disposed within a housing;
      the beam of radiation being directed to impinge upon a substantially horizontal support surface, supporting the emitter, at a location, and
      the location being approximately three meters from the emitter when a base associated with the emitter is disposed on the support surface and the housing is supported by the base, wherein
         a mount is supported by the base, and
         the base and the mount are configured to maintain the emitter at a fixed vertical height from the support surface when the beam impinges the support surface;
      receiving a first input based at least in part on the beam impinging the support surface;
      causing a display of a vision screening device to output an image included in a visual acuity examination based at least in part on the first input;
      receiving a second input based at least in part on the image; and
      determining a visual acuity of the patient based at least in part on the second input.

17. The system of claim 16, wherein the one or more processors comprises one or more components of a controller of the vision screening device, and the controller is configured to cause the light source to generate the beam based at least in part on a third input received via the vision screening device.

18. The system of claim 16, wherein the beam comprises a first beam, and the location comprises a first location, the operations further comprising causing the light source to generate a second beam of visible radiation,
   the second beam impinging the support surface at a second location approximately one meter from the emitter when the base is disposed on the support surface and the emitter is supported by the base, and
   the emitter maintaining a fixed position relative to the support surface when emitting the first beam and the second beam.

19. The system of claim 16, wherein the housing is removably connected to the base via the mount.

20. The system of claim 19, further comprising a stem movably connected to the mount, the vision screening device being removably connected to the stem such that the movement of the stem in a direction away from the support surface while the base is disposed on the support surface causes commensurate movement of the vision screening device away from the support surface.

21. The system of claim 19, further comprising a stem moveably connected to the base via the mount,
   the emitter being removably connected to the stem such that movement of the stem in a direction away from the support surface while the base is disposed on the support surface causes commensurate movement of the emitter and the vision screening device away from the support surface.

22. The system of claim 16, wherein the housing comprises a housing of the vision screening device, the system further comprising a stem movably connected to the base, wherein:
   the housing is removably connected to the stem via a coupling,
   the coupling includes a first electrical connector, and
   the housing includes a second electrical connector configured to mate with the first electrical connector when the housing is removably connected to the stem.

23. A method, comprising:
- receiving, with a controller, information indicating that a first electrical connector associated with a base has been mated with a second electrical connector of a vision screening device, the base being configured to support the vision screening device thereon;
- determining, by the controller, that a first connection parameter associated with the first electrical connector matches a second connection parameter associated with the second electrical connector;
- based at least in part on determining that the first connection parameter matches the second connection parameter, causing, with the controller, a light source of an emitter to generate a beam of visible radiation,
  - the beam of radiation being directed to impinge upon a substantially horizontal support surface, at a location, and
  - the location being approximately three meters from the emitter when the base is disposed on the support surface and the emitter is supported by the base;
- receiving, with the controller, a first input based at least in part on the beam impinging the support surface;
- causing, with the controller, a display of a vision screening device to output an image included in a visual acuity examination based at least in part on the first input;
- receiving, with the controller, a second input based at least in part on the image; and
- determining, with the controller, a visual acuity of the patient based at least in part on the second input.

24. The method of claim 23, wherein the first input is indicative of the patient being disposed at the location, and the second input is indicative of a response to the image by the patient, the method further comprising:
- receiving a third input with the controller and via the vision screening device; and
- causing, with the controller, the light source to generate the beam based at least in part on the third input.

25. The method of claim 23, wherein the first input is indicative of the patient being disposed at the location, the second input is indicative of a response to the image by the patient, the beam comprises a first beam, and the location comprises a first location, the method further comprising:
- receiving a third input with the controller and via the vision screening device; and
- causing, with the controller, the light source to generate a second beam of visible radiation based at least in part on the third input,
  - the second beam impinging the support surface at a second location approximately one meter from the emitter when the base is disposed on the support surface and the emitter is supported by the base, and
- the emitter maintaining a fixed position relative to the support surface when emitting the first beam and the second beam.

26. The method of claim 25, further comprising:
- causing, with the controller, an additional display of the vision screening device to output first instructions associated with the patient while the first beam impinges the support surface; and
- causing, with the controller, the additional display to output second instructions associated with the patient while the second beam impinges the support surface.

27. The method of claim 23,
- the first electrical connector comprising an electrical connector of a stem, the stem being movably connected to the base and configured to support the vision screening device on the base.

28. The method of claim 27, further comprising providing at least one of an audible or a visible an indication, via the vision screening device, that the first connection parameter matches the second connection parameter.

* * * * *